US010603677B2

(12) United States Patent
Dorian

(10) Patent No.: US 10,603,677 B2
(45) Date of Patent: Mar. 31, 2020

(54) RED BLOOD CELL WASHING SYSTEM

(71) Applicant: Randel E. Dorian, San Diego, CA (US)

(72) Inventor: Randel E. Dorian, San Diego, CA (US)

(73) Assignee: Hanuman Medical, San Francisco, CA (US)

( * ) Notice: Subject to any disclaimer, the term of this patent is extended or adjusted under 35 U.S.C. 154(b) by 102 days.

(21) Appl. No.: 15/828,483

(22) Filed: Dec. 1, 2017

(65) Prior Publication Data

US 2018/0154374 A1 Jun. 7, 2018

Related U.S. Application Data

(60) Provisional application No. 62/508,837, filed on May 19, 2017, provisional application No. 62/429,316, filed on Dec. 2, 2016.

(51) Int. Cl.

| | |
|---|---|
| ***B04B 5/04*** | (2006.01) |
| ***B04B 1/16*** | (2006.01) |
| ***B04B 11/08*** | (2006.01) |
| *B04B 1/04* | (2006.01) |

(52) U.S. Cl.

CPC .............. *B04B 5/0442* (2013.01); *B04B 1/16* (2013.01); *B04B 5/0407* (2013.01); *B04B 11/082* (2013.01); *A61M 2202/0429* (2013.01); *B04B 1/04* (2013.01)

(58) Field of Classification Search

CPC ........... B04B 1/04; B04B 1/16; B04B 5/0407; B04B 5/0442; B04B 11/082; A61M 2202/0429

See application file for complete search history.

(56) References Cited

U.S. PATENT DOCUMENTS

| | | | |
|---|---|---|---|
| 3,080,108 | A | 3/1963 | Jacobson |
| 4,854,933 | A | 8/1989 | Mull |

(Continued)

OTHER PUBLICATIONS

"U.S. Appl. No. 15/828,481, Notice of Allowance dated Apr. 29, 2019", 8 pgs.

(Continued)

*Primary Examiner* — Timothy C Cleveland

(74) *Attorney, Agent, or Firm* — Schwegman Lundberg & Woessner, P.A.

(57) ABSTRACT

A blood washing system including a rotor defining an internal chamber and a skimmer assembly configured to move a withdrawal needle within the internal chamber. A multi-component fluid, such as a whole blood sample, can be fed into the internal chamber via a feed tube, where the rotor can be rotated to fractionate the multi-component fluid. A brake can be applied to the rotor to cease rotation or rotated at a slower speed to allow the fractions of the multi-component to settle on a bottom wall of the rotor. The withdrawal needle is moveable within the internal chamber to align an orifice of the withdrawal needle for withdrawing the liquid fractions and isolate the solid fractions. Wash fluids can be added to the internal chamber to repeat the wash cycle without removing the solid fractions. The washed solid fractions can be withdrawn via the feed tube and collected.

18 Claims, 20 Drawing Sheets

X-X 38 46 24 20 52 56 54 32 22 48 30 36 28 34 26 42 40 44 50

(56) References Cited

U.S. PATENT DOCUMENTS

| | | | | |
|---|---|---|---|---|
| 6,544,162 | B1 * | 4/2003 | Van Wie ............ | A61M 1/3693 494/35 |
| 8,540,078 | B2 | 9/2013 | Leach et al. | |
| 2008/0011684 | A1 | 1/2008 | Dorian et al. | |
| 2015/0024922 | A1 * | 1/2015 | Castillo Gonzalez ...................... | B04B 5/0442 494/40 |
| 2018/0154286 | A1 | 6/2018 | Dorian | |
| 2018/0154373 | A1 | 6/2018 | Dorian | |

OTHER PUBLICATIONS

"U.S. Appl. No. 15/828,485, Response filed Jul. 18, 2019 to Restriction Requirement dated May 21, 2019", 7 pgs.

"U.S. Appl. No. 15/828,485, Restriction Requirement dated May 21, 2019", 8 pgs.

U.S. Appl. No. 15/828,481, filed Dec. 1, 2017, Blood Washing and Separation System.

U.S. Appl. No. 15/828,485, filed Dec. 1, 2017, Red Blood Cell Elutriation Wash System.

* cited by examiner

RED BLOOD CELL WASHING SYSTEM

CLAIM OF PRIORITY

This patent application claims the benefit of priority, under 35 U.S.C. Section 119(e), to Randel E. Dorian, U.S. Patent Application Ser. No. 62/429,316, entitled "BLOOD WASHING AND SEPARATION SYSTEM," filed on Dec. 2, 2016, and Randel E. Dorian, U.S. Patent Application Ser. No. 62/508,837, entitled "BLOOD WASHING AND SEPARATION SYSTEM," filed on May 19, 2017, each of which is hereby incorporated by reference herein in its entirety.

TECHNICAL FIELD

This document pertains generally, but not by way of limitation, to washing systems for red blood cells and other cellular materials.

BACKGROUND

Whole blood samples are often fractionated to separate red blood cells, platelets, and other cellular materials from the plasma and other fluid components of the whole blood. A selected fraction, typically red blood cells or cellular materials, can be selectively withdrawn from the fractionated whole blood sample for use in certain medical applications. The isolated cellular material is often further processed by adding one or more wash fluids to the isolated cellular materials to remove any plasma or other undesirable fluids or materials clinging to or intermixed with the desired cellular material. The resulting wash solution comprising cellular material within the wash fluids is often fractionated again to separate and isolate the cellular material from the wash fluids.

For certain medical applications, the cellular materials must often be washed multiple times to cleanse the cellular material to certain predetermined standards. However, each wash cycle requires the addition of new wash fluids, fractionation of the wash solution, and isolation of the cellular materials from the wash fluids, which is time-consuming and is often labor intensive. Also, as the wash solution is typically centrifuged to fractionate the wash solution, separate containers must be connected to add or withdraw wash solution from the centrifuge rotor before being disconnected to permit rotation of the centrifuge rotor for fractionation. The repeated connection and disconnection of separate containers can increase the risk of contamination or degradation of cellular material within the centrifuge rotor.

OVERVIEW

The present inventors have recognized, among other things, that a problem to be solved can include efficiently washing cellular material without excessive risk of contamination or degradation of the cellular material. In an example, the present subject matter can provide a solution to this problem, such as by providing a rotor defining an internal chamber for receiving a multi-component fluid and a skimmer assembly including a moveable withdrawal needle for selectively withdrawing separated fractions of the multi-component fluid. The multi-component fluid can be fed into the internal chamber through a feed tube before the rotor can be rotated at a first speed to fractionate the multi-component fluid. A brake can be applied to the rotor to slow rotation of the rotor to a slower second speed or stop rotation of the rotor, which can cause the solid fractions and denser fluid fractions to settle on the bottom wall of the rotor. The withdrawal needle can be moved within the internal chamber to align an orifice of the withdrawal needle with a selected fraction, which can be withdrawn from the internal chamber through the withdrawal needle to isolate the fractions retained within the rotor. Additional fluids, such as additional wash fluids, can be added to the isolated fractions within the internal chamber through the feed tube before rotation of the rotor at the first speed to fractionate the wash solution for withdrawal of the wash fluids. After the targeted fractions have been sufficiently washed, the targeted fractions can be withdrawn from the internal chamber through the feed tube and collected.

In an example, the rotor can be positioned within a rotor chamber defined by an outer housing. The feed tube and a withdrawal tube of the skimmer assembly can extend through the outer housing to the rotor. The rotor can include an access port permitting the feed tube and the withdrawal tube to extend into the internal chamber of the rotor. The access port can be sized to permit the rotor to rotate around the feed tube and withdrawal tube without contacting the tubes or requiring at least one of the tubes to be fixed to the rotor. The outer housing can isolate the rotor to prevent contaminants from entering the rotor chamber and the internal chamber of the rotor through the access port. In this configuration, the rotor can be rotated within the outer housing whereas the outer housing removes the need for an expensive and often leaky rotatable connection between the withdrawal tube or the feed tube and the rotor. In an example, the rotor can include integrated magnets or other mechanisms permitting rotation of the rotor within the outer housing. The outer housing can include a bearing for facilitating rotation of the rotor within the outer housing.

A skimmer-less blood washing system, according to an example of the present disclosure, can include a rotor comprising a radial wall extending from an upper wall to a lower wall to define an internal chamber. The rotor can include a withdrawal tube connected to a withdrawal port positioned at the bottom of the internal chamber. The rotor can include an access tube extending through the upper wall and fluidly connected to an access port positioned at the top or the bottom of the internal chamber. The radial wall can include an inwardly projecting shelf positioned at the top or bottom of the internal chamber corresponding to the position of the access port. The inwardly projecting shelf can define a reduced diameter portion at the top of the internal chamber positioned over a primary portion defined by the radial wall, wherein the access port is positioned to fluidly connect with the reduced diameter portion.

In an example, a multi-component fluid can be provided through the access tube and into the internal chamber via the access port. The rotor can be rotated at a first speed to fractionate the multi-component fluid. A brake can be applied to the rotor to slow rotation of the rotor to a slower second speed or stop rotation of the rotor, which can cause the solid fractions and denser fluid fractions to settle on the bottom wall of the rotor. Lighter fractions and excess wash fluid can be aspirated off through the access port, wherein an empty head space is formed in the reduced diameter portion above the solid fractions and denser fluid fractions retained within the primary portion of the internal chamber. Aspirating the wash fluids off through the access port avoids or reduces disruption of the solid fractions (e.g. red blood cell pellets) and denser fluid fractions retained in the primary portion of the internal chamber. In an example, the rotor can be rotated at a slower rotational speed during aspiration. Additional wash fluids can be provided into the internal chamber through the access port through the empty head-space provided by the reduced diameter portion at the top of the internal chamber or percolated through the solid or denser fluid fractions from the bottom of the internal chamber. Following washing, the solid and denser fluid fractions can be withdrawn from the internal chamber through the withdrawal port at the bottom of the internal chamber.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
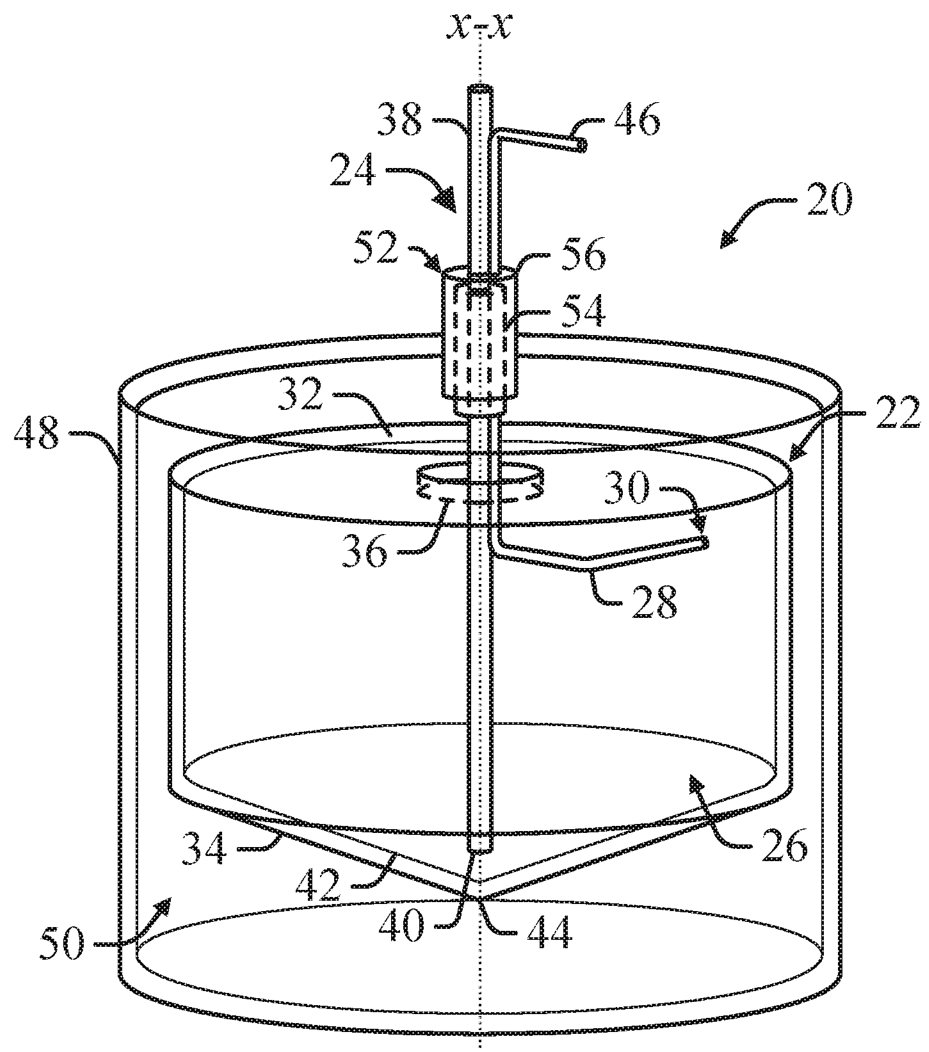
FIG. 1 is a schematic side perspective view of a blood washing system according to an example of the present disclosure.
Figure 2:
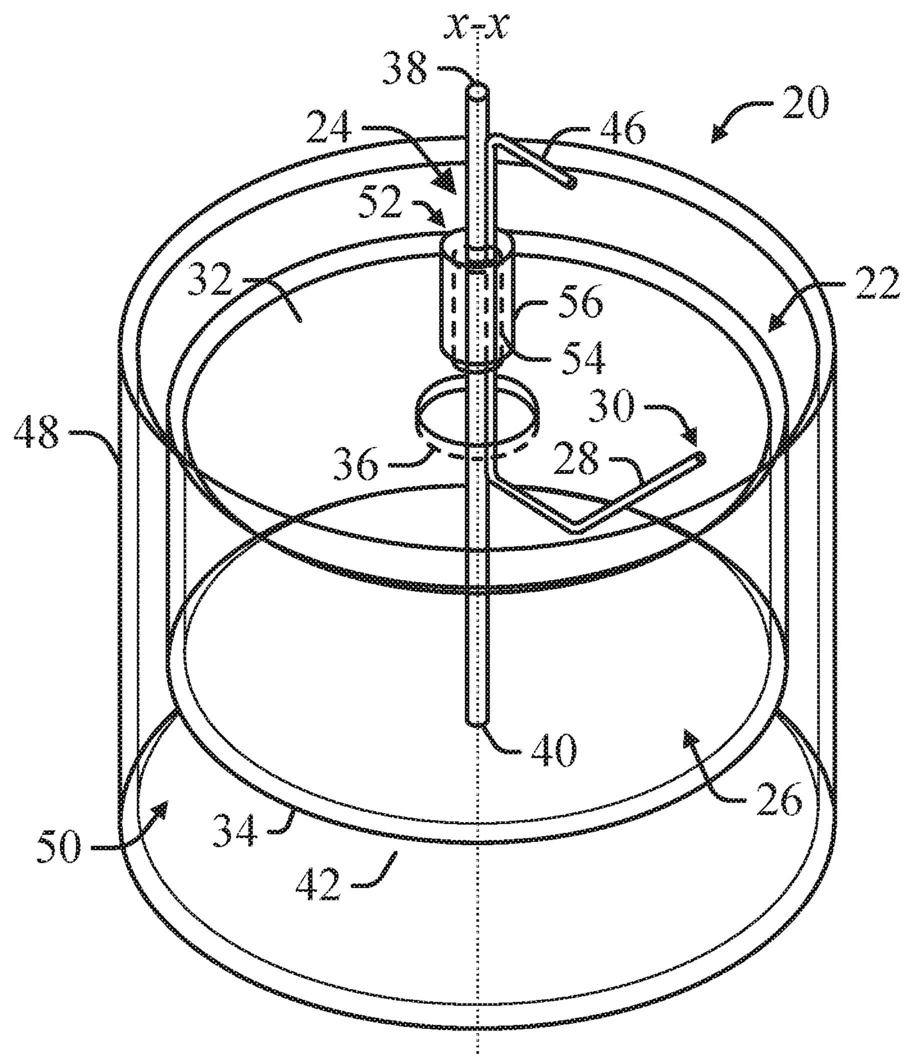
FIG. 2 is a schematic top perspective view of the blood washing system of FIG. 1.

As depicted in FIGS. 1-2, a blood washing system 20 for washing cellular material, according to an example, can include a rotor 22 for fractionating a multi-component fluid and a skimmer assembly 24 for withdrawing a selected fraction of the multi-component fluid from the rotor 22. The rotor 22 can define an internal chamber 26 for receiving a multi-component fluid, such as a whole blood sample, a wash solution comprising cellular material suspended in a wash fluid, or other multi-component fluids containing solid material suspended in a fluid. The rotor 22 can be rotated about a rotational axis x-x to fractionate the multi-component fluid into a plurality of fractions. The plurality of fractions can comprise at least one solid fraction containing the solid material and at least one liquid fraction containing the liquid material. In certain examples, the plurality of fractions can comprise multiple liquid fractions having a different density. The skimmer assembly 24 can include a moveable withdrawal needle 28 having an orifice 30 that can be positioned within a selected fraction and withdraw the selected fraction (e.g. a liquid fraction) from the internal chamber 26 to isolate the fractions remaining within the internal chamber (e.g. a solid fraction). In an example, the withdrawal needle 28 can be repositioned within the internal chamber such that the orifice 30 is positioned within a different fraction to draw the different fraction from the internal chamber 26 to further isolate the remaining fractions.

Figure 3A:
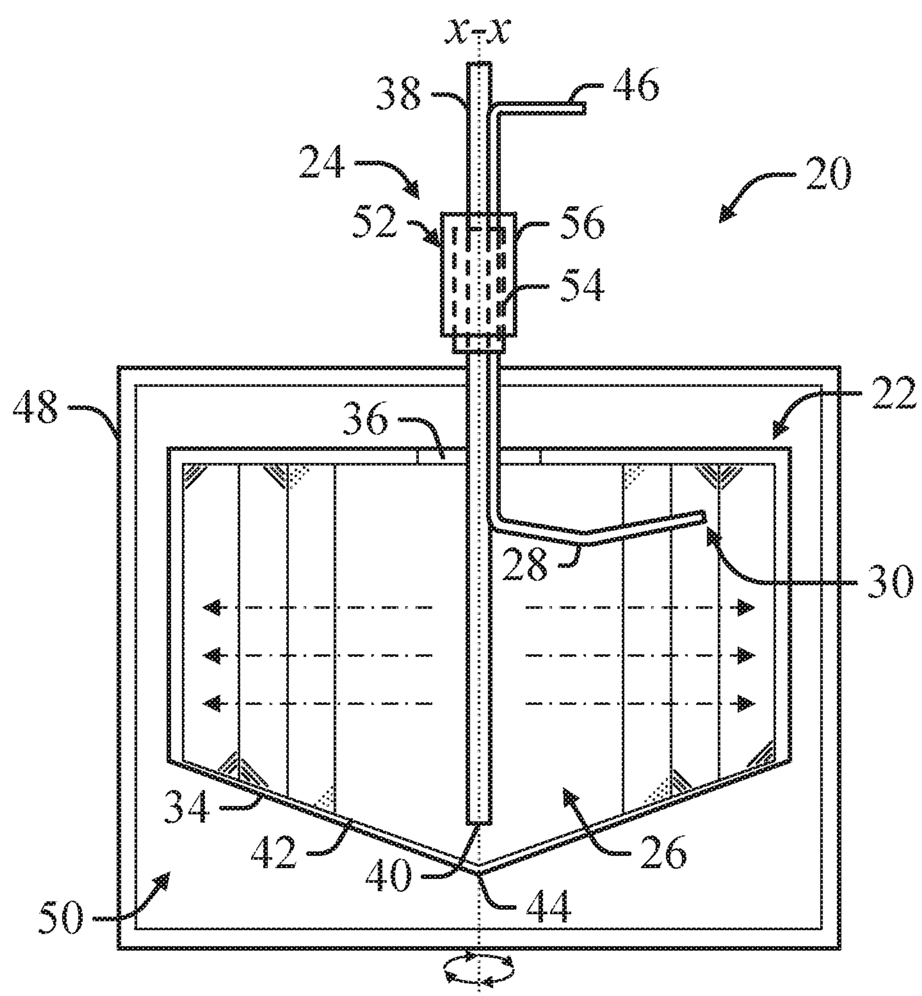
FIG. 3A is a schematic side view of a blood washing system during rotation of a rotor to fractionate a multi-component fluid within the rotor according to an example of the present disclosure.
Figure 3B:
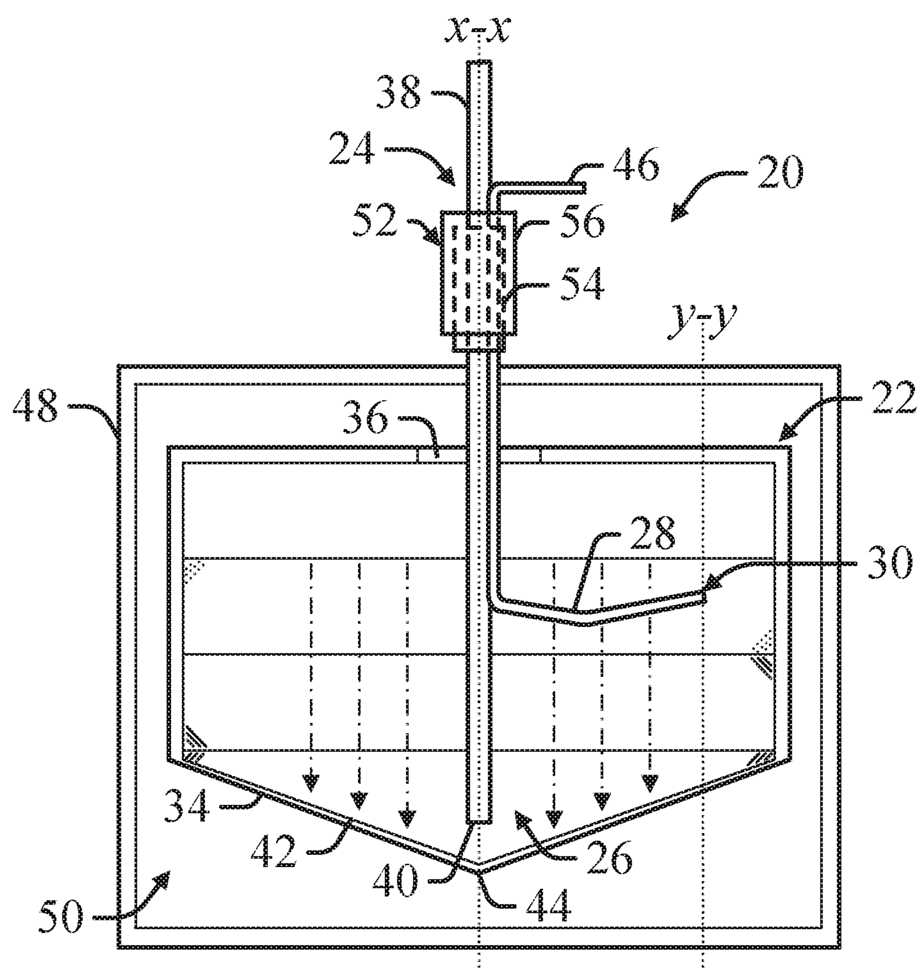
FIG. 3B is a schematic side view of a blood washing system during breaking or slower rotation of a rotor to settle fractionated components of a multi-component fluid within the rotor according to an example of the present disclosure.

As depicted in FIGS. 1-2 and 3A-B, in an example, the rotor 22 can further include a top wall 32 and a bottom wall 34. The top wall 32 can define an access port 36 for accessing the internal chamber 26. In an example, the blood washing system 20 can include a feed tube 38 having a feed orifice 40 that can be inserted into the internal chamber 26 through the access port 36. The feed tube 38 can be used to feed the multi-component fluid into the internal chamber 26. The feed tube 38 can be positioned within the rotor 22 such that the feed orifice 40 is proximate the bottom wall 34 of the rotor 22. In this position, the feed tube 38 can withdraw denser fluid or solid fractions of the multi-component fluid that settles on the bottom wall 34 of the rotor 22 following fractionation. As depicted in FIGS. 3A-3B, in an example, the bottom wall 34 can have a tapered floor 42 sloped toward a bottom apex 44. The feed orifice 40 can be positioned proximate the bottom apex 44 such that the tapered floor 42 funnels denser fluid or solid fractions toward the bottom apex 44 as the material is withdrawn through the feed tube 38. In certain examples, the rotational axis x-x intersects the bottom apex 44.

As illustrated in FIGS. 3A-B, in operation, a multi-component fluid can be fed into the internal chamber 26 through the feed tube 38. The multi-component fluid can include but is not limited to a whole blood sample, a wash solution comprising cellular material suspended in a wash fluid, or other multi-component fluids containing solid material suspended in a fluid. As illustrated in FIG. 3A, the rotor 22 can be rotated about the rotational axis x-x at a first speed to fractionate the multi-component fluid within the internal chamber 26 into a plurality of fractions. The denser fluid and solid fractions are pushed further outward radially from the rotational axis x-x by the rotation of the rotor 22 while the less dense fluid fractions remain closer to the rotational axis x-x. A brake can be applied to the rotor 22 to stop rotation of the rotor 22 or to rotate the rotor 22 at a second speed slower than the first speed causing the fractions to settle within the internal chamber 26 with the denser fluids and solids settling toward the bottom wall 34. The denser fluids and solids of the fractionated components settle toward the bottom wall 34 where the lighter fluids of the fractionated components settle above the denser fractionated components.

As illustrated in FIG. 3B, the skimmer assembly 24 can be operated to move the withdrawal needle 28 along movement axis y-y to align the withdrawal orifice 30 with a selected fraction for withdrawing the selected fraction from the internal chamber 26 through the withdrawal needle 28 to isolate the remaining fraction(s) within the internal chamber 26. The withdrawal needle 28 can be coupled to a withdrawal outlet 46 positioned externally of the rotor 22, where a container (not shown) can be coupled to the withdrawal outlet 46 to receive the withdrawn selected fraction. While withdrawing a selected fraction, the withdrawal needle 28 can be moved proximate a boundary between adjacent fractions to draw the entire selected fraction from the internal chamber 26. In certain examples, the withdrawal needle 28 can be moved a second time to align the withdrawal orifice 30 with a second fraction to withdraw the second fraction. Additional fluid, such as wash fluids, can be added to the internal chamber 26 through the feed tube 38 after the selected fraction(s) have been withdrawn. The rotor 22 can then be rotated to fractionate the new solution and withdraw selected fractions (e.g. contaminated wash fluids). The process can be repeated to wash a targeted fraction multiple times. Following wash cycle(s) and withdrawal of undesired fractions, the feed tube 38 can be used to draw the targeted fraction (e.g. cellular material) from the internal chamber 26.

In an example, the blood washing system 20 can be a multi-wash system for washing red blood cells where a whole blood sample or an initial wash solution having red blood cells suspended within wash fluids is fed into the internal chamber 26 through the feed tube 38. The rotor 22 can be rotated at a first speed to fractionate the whole blood sample or initial wash solution to separate the solution into at least a solid fraction containing the red blood cells and a liquid fraction. A brake can be applied to the rotor 22 to stop rotation of the rotor 22 or rotated at the slower second speed to cause the cellular material to settle on the bottom wall 34 of the rotor 22 with the fluid components floating about the cellular material. A brake can be applied to the rotor 22 to stop rotation of the rotor 22 or rotated at a second speed slower than the first speed causing the solid fraction to settle on the bottom wall 34 of the rotor 22 with the fluid fraction floats above the solid fraction. The skimmer assembly 24 can be operated to move the withdrawal needle 28 along movement axis y-y to align the withdrawal orifice 30 with a selected fraction for withdrawing the fluid fraction from the internal chamber 26 through the withdrawal needle 28 to isolate the solid fraction within the internal chamber 26. Additional fluids, such as wash fluids, can be added through the feed tube 38 to the isolated solid fraction within the internal chamber 26. The process can then be repeated to remove waste fluids from the rotor 22 until the cellular material is sufficiently washed. The washed and isolated solid fraction can be withdrawn from the internal chamber 26 through the feed tube 38 following washing.

As depicted in FIGS. 1-4, in an example, the blood washing system 20 can include an outer housing 48 defining a rotor chamber 50 for receiving the rotor 22. The rotor chamber 50 can isolate the rotor 22 where the feed tube 38 and the withdrawal needle 28 extend through the outer housing 48 and enter the internal chamber 26 through the access port 36 of the rotor 22. In an example, the feed tube 38 and/or the withdrawal needle 28 can have a fixed position, while the access port 36 is sized such that rotor 22 is rotatable around the feed tube 38 or withdrawal needle 28 without engaging or requiring movement of the feed tube 38 or withdrawal needle 28. In this configuration, an expensive and difficult to tightly seal rotational seal is not required between the feed tube 38 and the withdrawal needle 28 and the rotor 22. The outer housing 48 isolates the rotor 22 such that contaminants do not enter the access port 36. The rotor 22 can include integrated magnets for inducing rotation of the rotor 22 within the outer housing 48. The outer housing 48 can include bearings for supporting the rotor 22 as the rotor 22 is rotated about the rotational axis x-x. As depicted in FIGS. 1-4, the outer housing 48 encloses the rotor 22 to seal the rotor 22. In certain examples, any of configurations of the rotor 22 disclosed herein can be operated without the outer housing 48.

As depicted in FIGS. 1-3, in an example, the skimmer assembly 24 can include an adjustable hermetic seal 52 that fluidly connects the withdrawal needle 28 to the withdrawal outlet 46. The hermetic seal 52 can include an inner sleeve 54 connected to the withdrawal needle 28 and an outer sleeve 56 connected to the withdrawal outlet 46. The inner sleeve 54 can be slidably received within the outer sleeve 56 in an overlapping configuration. In operation, the withdrawal needle 28 can be moved along movement axis y-y causing the adjustable hermetic seal 52 to extend or contract while maintaining the fluid connection between the outer sleeve 56 and the inner sleeve 54.

Figure 4:
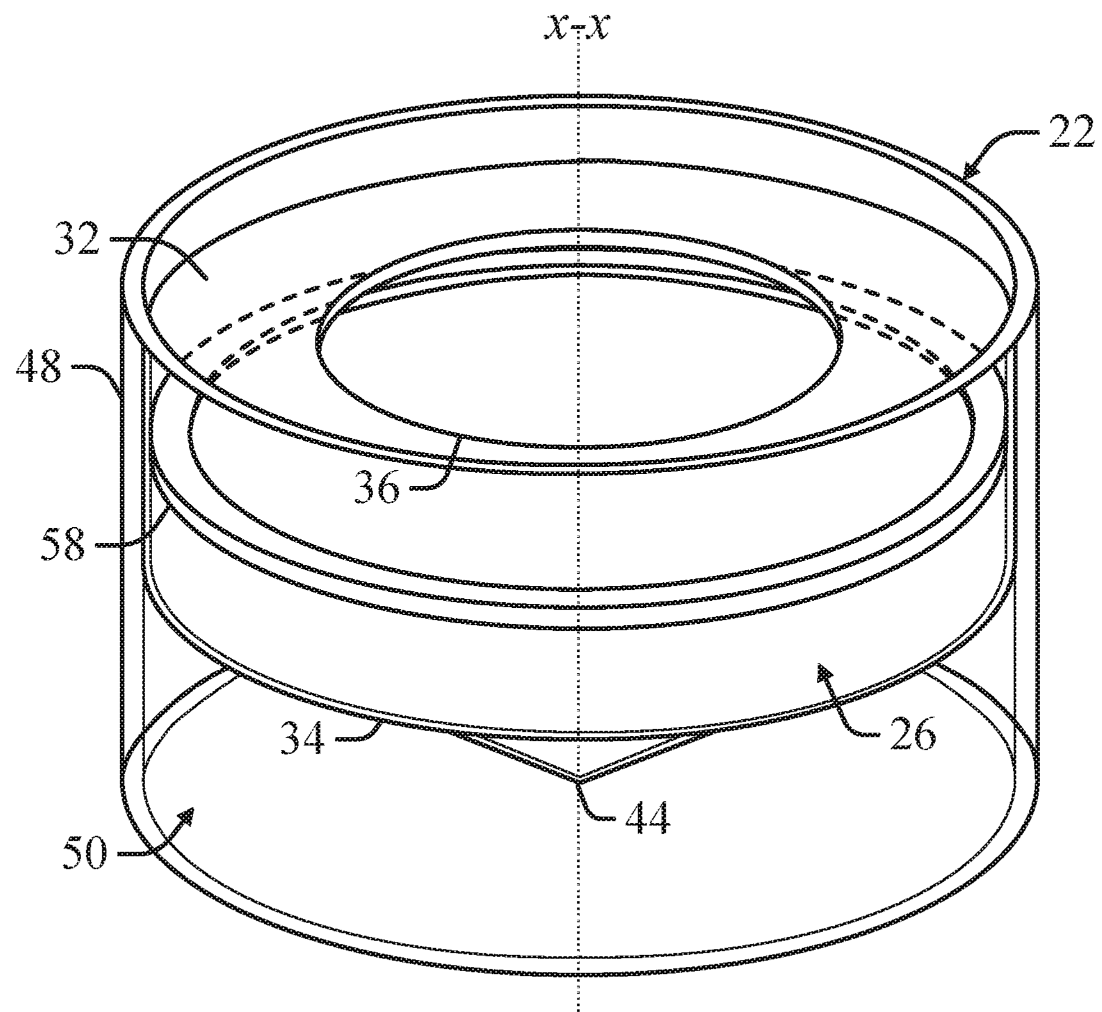
FIG. 4 is a schematic perspective view of the blood washing system having a washer guide according to an example of the present disclosure.

As depicted in FIG. 4, in an example, the rotor 22 can include a washer guide 58 positioned within the interior chamber 26 along an inner wall surface of the rotor 22. The washer 58 can be positioned on the inner wall surface to engage the withdrawal needle 28 as the withdrawal needle 28 moves along the movement axis y-y to limit the travel distance of the withdrawal needle 28. The washer 58 can be positioned to correspond to a boundary between fractions such that the washer 58 prevents the withdrawal needle 28 from a first fraction, crossing the boundary, and into an adjacent second fraction. The washer 58 can also lessen turbulence and intermix of fractions at the boundary between the adjacent fractions. The washer 58 permits the withdrawal needle 28 to be positioned against the washer 58 such that the withdrawal orifice 30 is proximate the boundary between the fractionated components to maximize withdrawal of the first fraction while minimizing the risk that the withdrawal orifice 30 will inadvertently enter the second fraction. The washer 58 can be mounted on the inner wall surface of the rotor 22 at a fixed position predetermined to approximate a boundary between adjacent fractions. The washer guide 58 can be free floating and having a predetermined buoyancy such that the washer guide 58 floats proximate the boundary between the adjacent fractionated components.

Figure 5:
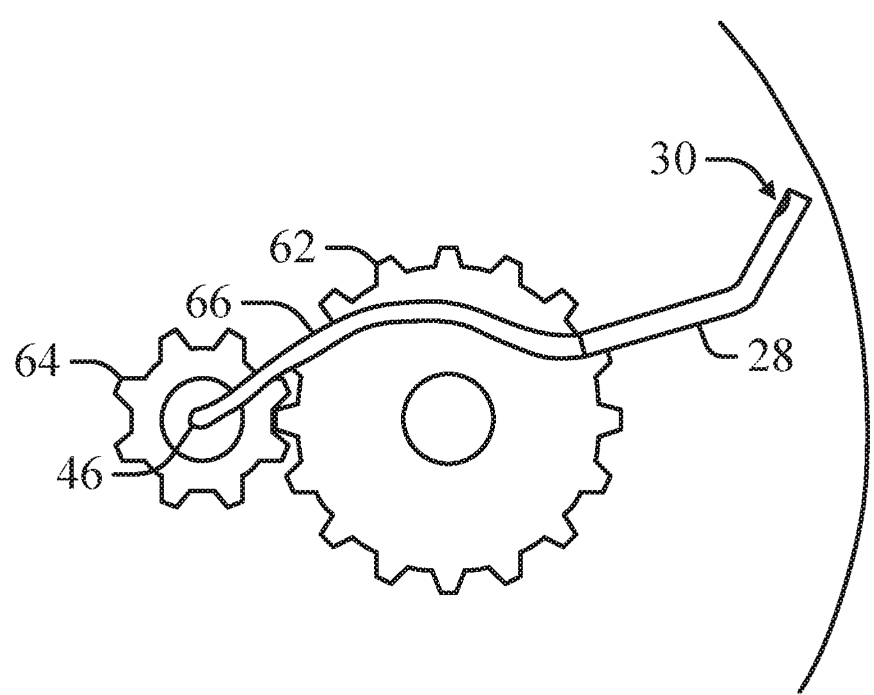
FIG. 5 is a schematic top view of a skimmer assembly according to an example of the present disclosure.
Figure 6:
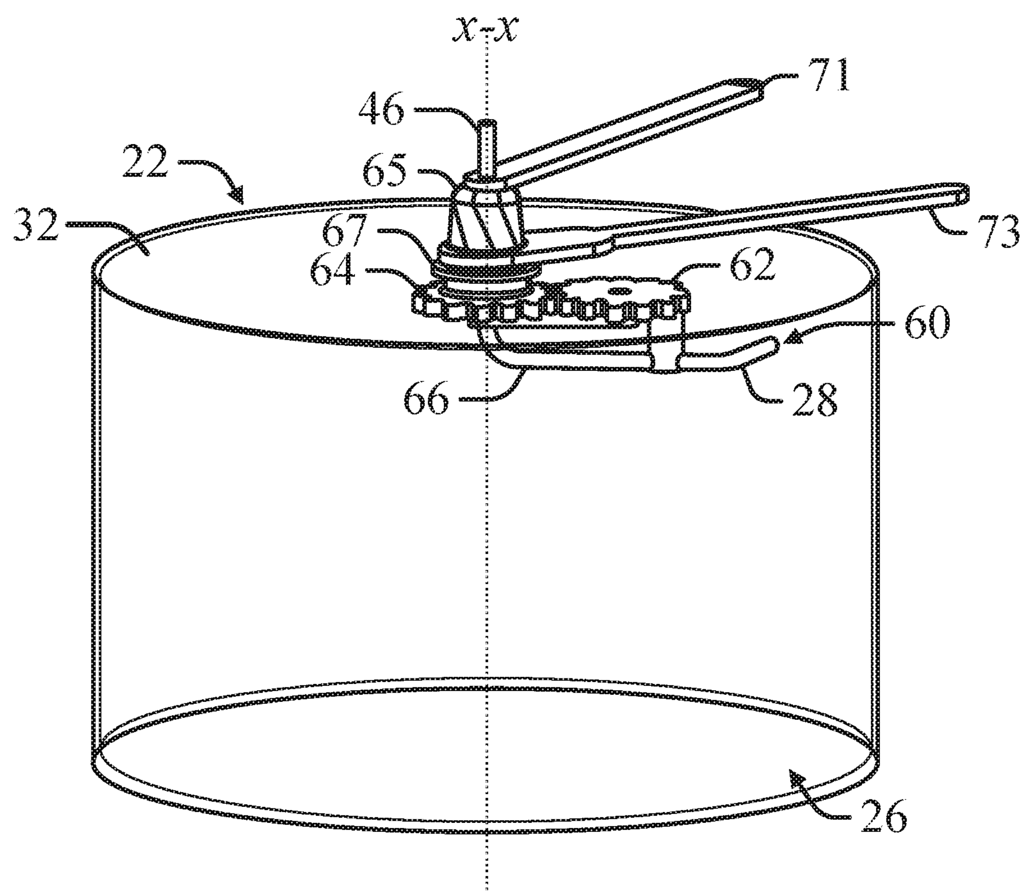
FIG. 6 is a schematic perspective view of a blood washing system having a rotatable withdrawal needle according to an example of the present disclosure.
Figure 7:
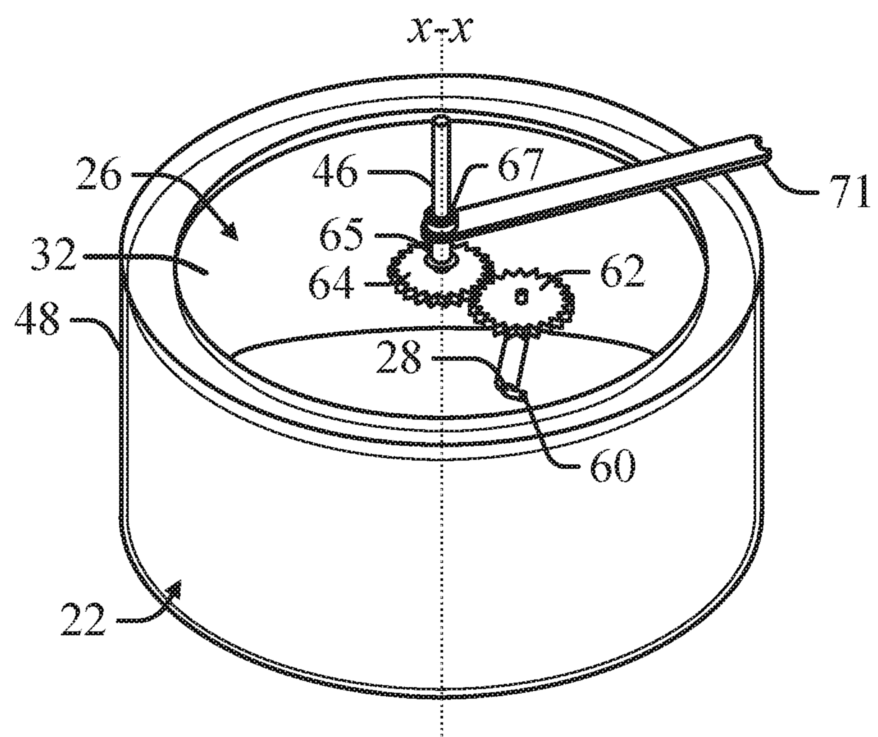
FIG. 7 is a schematic perspective view of a blood washing system having a rotatable withdrawal needle according to an example of the present disclosure.

In an example, the rotor 22 can be rotated at the slower second speed to cause the fractions of the multi-component fluid within the internal chamber 26 to flow within the rotor 22 about the rotational axis x-x. In this configuration, the withdrawal orifice 30 can comprise a scoop shape oriented transverse to the flow of the multi-component fluid to collect a selected fraction as the fraction flows within rotor 22. As depicted in FIGS. 5-7, in an example, the skimmer assembly 24 can comprise a skimmer arm 60 positioned on a slave gear 62, wherein the withdrawal needle 28 is positioned on the slave gear 62 to rotate with the slave gear 62. In this configuration, the slave gear 62 can be intermeshed with a drive gear 64 such that rotation of the drive gear 64 rotates the slave gear 62 and the mounted on the slave gear 62. In this configuration, the withdrawal needle 28 can be rotated by the slave gear 62 to collect a selected fraction. In a certain direction, the rotor 22 can be rotated at the slower speed in an opposing direction to direct the flow of fluid in the opposing direction to facilitate the collection of the selected fraction. In an example, the slave gear 62 has a first diameter while the drive gear 64 has a smaller diameter than the first diameter.

As depicted in FIGS. 6 and 7, in an example, the skimmer assembly 24 can further include a twist seal 65 rotatably positioned on the withdrawal outlet 46. The twist seal 65 can be rotated around the withdrawal outlet 46 to compress a gasket 67 between the twist seal 65 and the rotor 22 or the outer housing 62 to prevent leakage past the twist seal 65. The twist seal 65 can also include a rotatable seal within the twist seal 65 between the twist seal 65 body and the withdrawal outlet 46 to prevent leakage along the withdrawal outlet 46. In an example, the twist seal 65 can include a control lever 71 that can be gripped for rotating the twist seal 65 and apply pressure to the gasket 67. As depicted in FIG. 6, a hold lever 73 can be positioned on the twist seal 65 to maintain positioning of the twist seal 65 on the withdrawal outlet 46 while the twist seal 65 is rotated by pulling the control lever 71.

Figure 8:
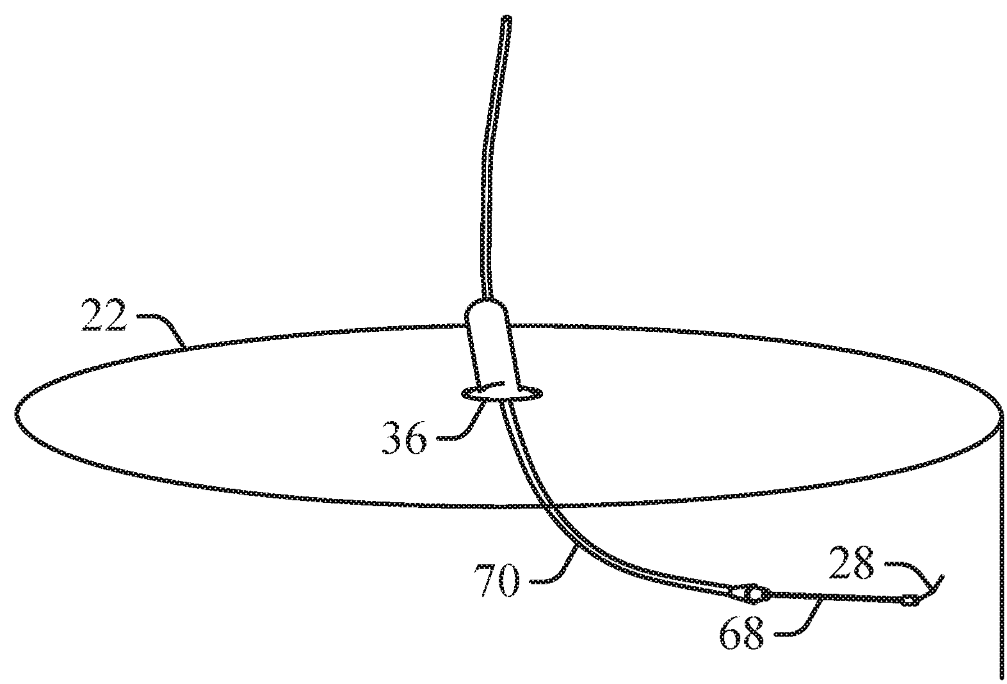
FIG. 8 is a schematic perspective view of a skimmer assembly according to an example of the present disclosure.

As depicted in FIGS. 6 and 8, in an example, the withdrawal needle 28 can be connected to the withdrawal outlet 46 by a flexible tube 66 such that the withdrawal needle 28 can be moved within the internal chamber 26 about a fixed withdrawal outlet 46. As depicted in FIG. 8, the skimmer assembly 24 can include a positioning cable 68 that can be coupled to the withdrawal needle 28. The positioning cable 68 can be extended and retracted axially to move the withdrawal needle 28 within the internal chamber 26. The positioning cable 68 can be slidably received within a rigid tube 70 for guiding the positioning cable 68 into the internal chamber 26 and directing the extension or retraction of the positioning cable 68. In an example, the rigid tube 70 can be shaped such that the extension or retraction of the positioning cable 68 moves the withdrawal needle 28 in at least one radially outer from the rotational axis, vertically within the internal chamber 26, or combinations thereof.

Figure 9A:
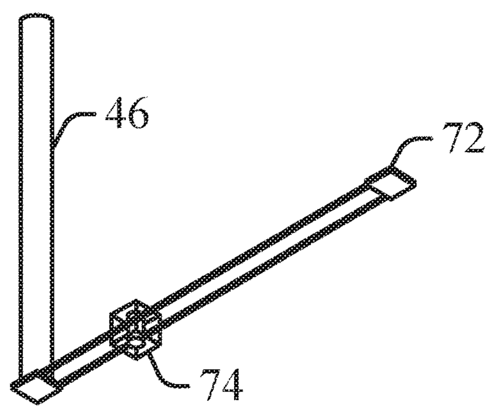
FIG. 9A is a schematic bottom view of a track of a skimmer assembly having a moveable external magnet positioned in a first position according to an example of the present disclosure.
Figure 9B:
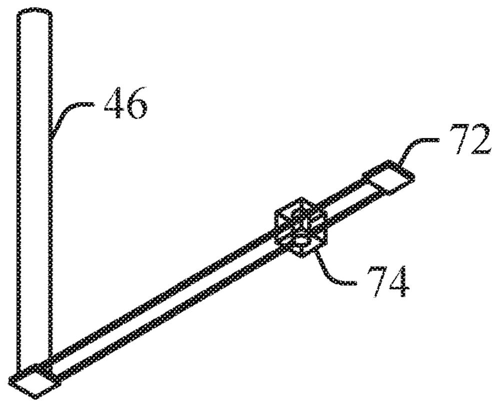
FIG. 9B is a schematic bottom view of a track of a skimmer assembly having a moveable external magnet positioned in a second position according to an example of the present disclosure.
Figure 9C:
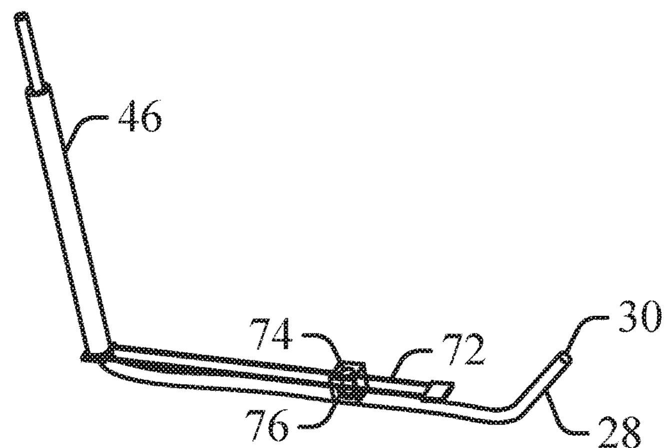
FIG. 9C is a schematic top view of a skimmer assembly according to an example of the present disclosure.

As depicted in FIGS. 9A-C, in an example, the skimmer assembly 24 can include an exterior track 72 positioned proximate an exterior face of the rotor 22 and an external magnet 74 moveable along the external track 72. An internal magnet 76 can be coupled to the withdrawal needle 28. The internal magnet 76 can be magnetically coupled to the external magnet 74 such that movement of the external magnet 74 moves withdrawal needle 28 within the internal chamber 26. In an example, the external track 72 can be oriented such that the external track 72 intersects the rotational axis x-x. In this configuration, the movement of the external magnet 74 along the external track 72 moves the withdrawal needle 28 radially about the rotational axis x-x. In an example, the external track 72 is fixedly mounted to at least one of the withdrawal outlet 46 and the feed tube 38 such that the external track 72 does not rotate with the rotor 22.

Figure 10:
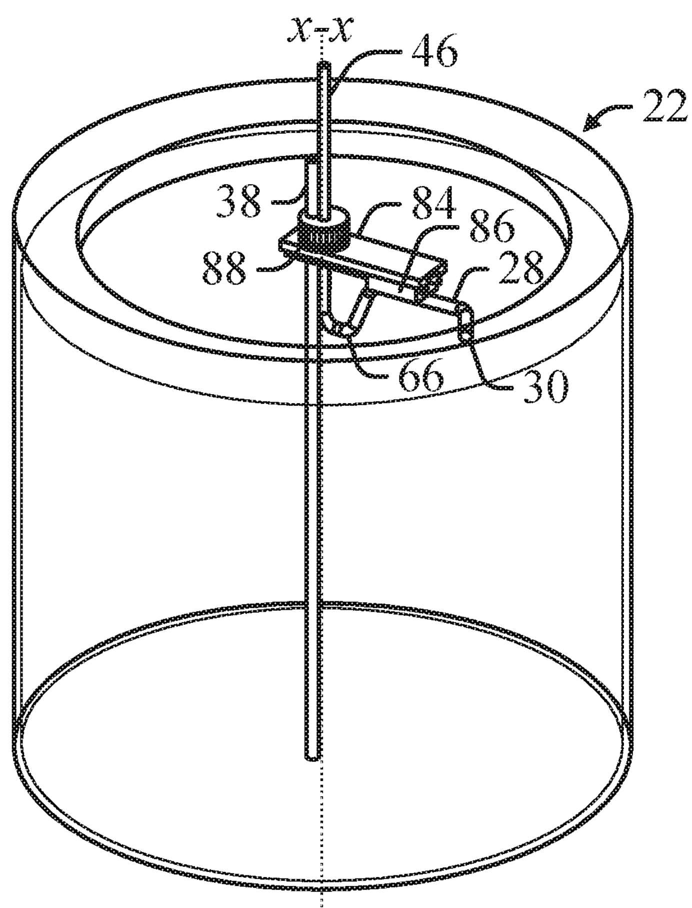
FIG. 10 is a schematic perspective view of a skimmer assembly according to an example of the present disclosure.

As depicted in FIG. 10, in an example, the skimmer assembly 24 can include a guide track 84 and can include a cart 86 slidably coupled to the interior track 84. The cart 86 can include an integrated magnet for moving the cart 86 along the guide track 84. In an example, the guide track 84 can be oriented such that the guide track 84 intersects the rotational axis x-x. In this configuration, the movement of the cart 86 along the guide track 84 moves the withdrawal needle 28 radially about the rotational axis x-x. The guide track 84 can be mounted to at least one of the withdrawal outlet 46 and the feed tube 38 such that the guide track 84 does not rotate with the rotor 22. A rotating seal 88 can be positioned around the feed tube 38 and the withdrawal outlet 46 above the guide track 84, where the rotating seal 88 can interface with the outer housing 48 to prevent leakage of fluids through the openings in the outer housing 48 for the feed tube 38 and the withdrawal outlet 46.

Figure 11A:
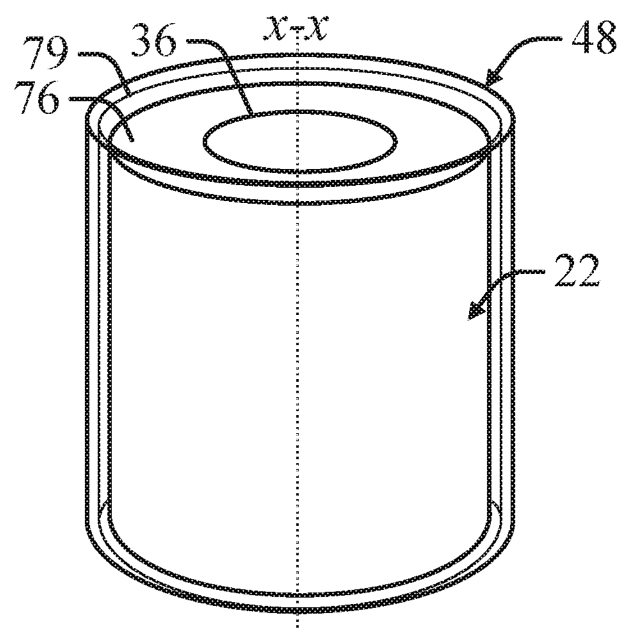
FIG. 11A is a schematic perspective view of a rotor within an outer housing wherein the rotor has a height greater than its width according to an example of the present disclosure.
Figure 11B:
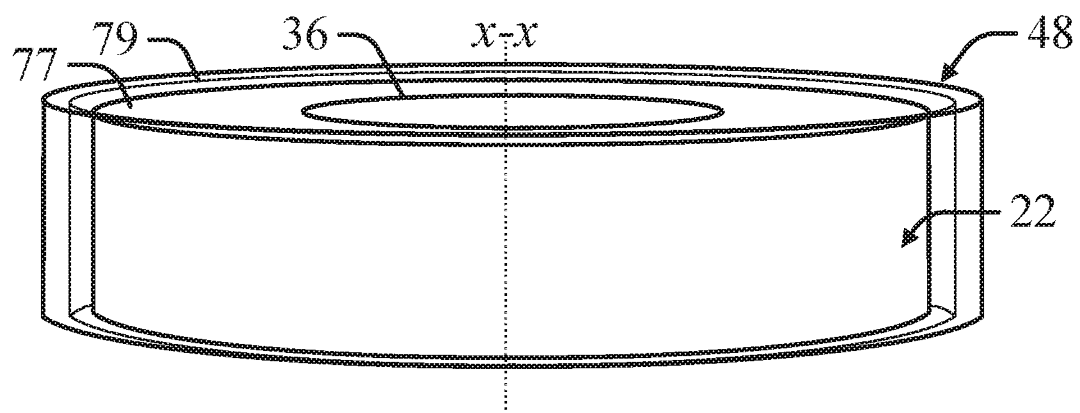
FIG. 11B is a schematic perspective view of a rotor within an outer housing wherein the rotor has a width greater than its height according to an example of the present disclosure.

The relationship of the height of the rotor 22 relative to the width of the rotor 22 can cause the rotor 22 to wobble when rotated at high speeds required to fractionate the multi-component fluid. If the height of the rotor 22 is greater than the width of the rotor 22 as illustrated in FIG. 11A, the rotor 22 can be more susceptible to high-speed wobble during rotation of the rotor 22. In this configuration, the rotor 22 can include an upper bearing surface 77 for contacting an inner surface 79 of the outer housing 48. The engagement of the upper bearing surface 77 of the rotor 22 to the inner surface 79 of the outer housing 48 maintains alignment of the rotor 22 during rotation of the rotor 22. If the height of the rotor 22 is less than the width of the rotor 22 as illustrated in FIG. 11B, the rotor 22 is less susceptible to high speed and can be rotated without contacting the upper surface 77 to the inner surface 79.

Figure 12:
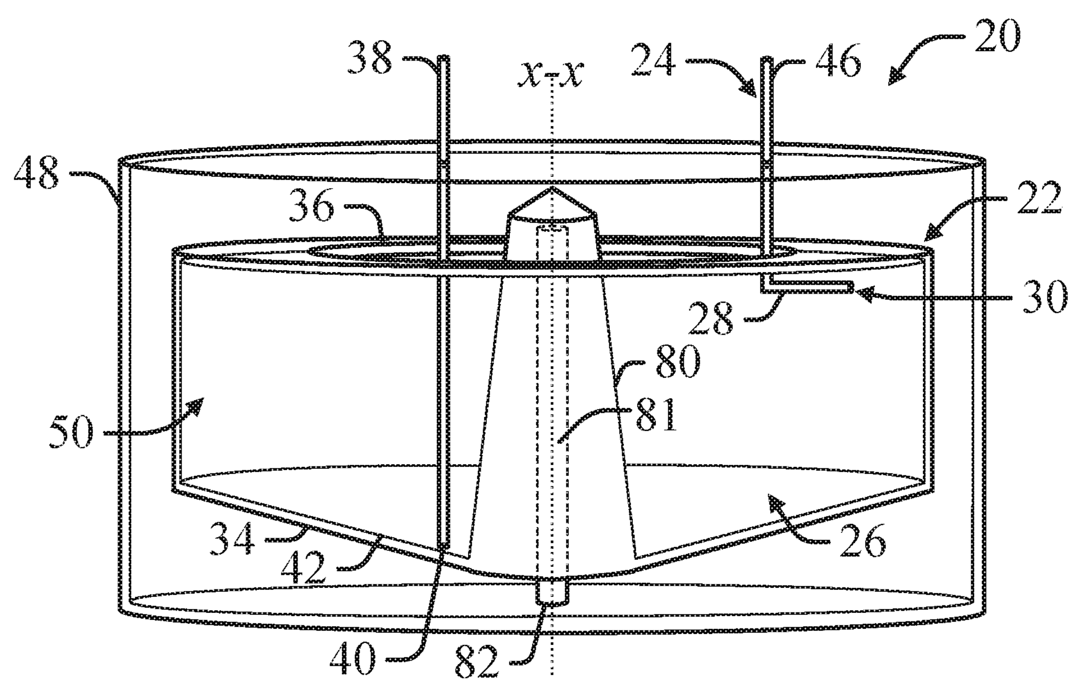
FIG. 12 is a perspective view of a rotor having a center post according to an example of the present disclosure.

As depicted in FIG. 12, in an example, the rotor 22 can include a center post 80 defining a central port 81 for receiving a spindle 82 extending from a bottom wall of the outer housing 48. The spindle 82 can be positioned on the bottom wall to extend along the rotational axis x-x. The spindle 82 can limit wobble of the rotor 22 during high-speed rotation and rotation about an axis offset from the rotational axis x-x. The center post 80 can define width forcing the multi-component fluid radially outward from the rotational axis x-x, which can reduce wobble during initial wind up of the rotor 22. In an example, the spindle 82 can be attached to the rotor 22 such that the spindle 82 can be rotated by the rotor 22. In this configuration, additional tubes or connectors can be inserted into the internal chamber 26. The additional tubes or connectors can be positioned within the internal chamber 26 offset from the central post 80.

Figure 13:
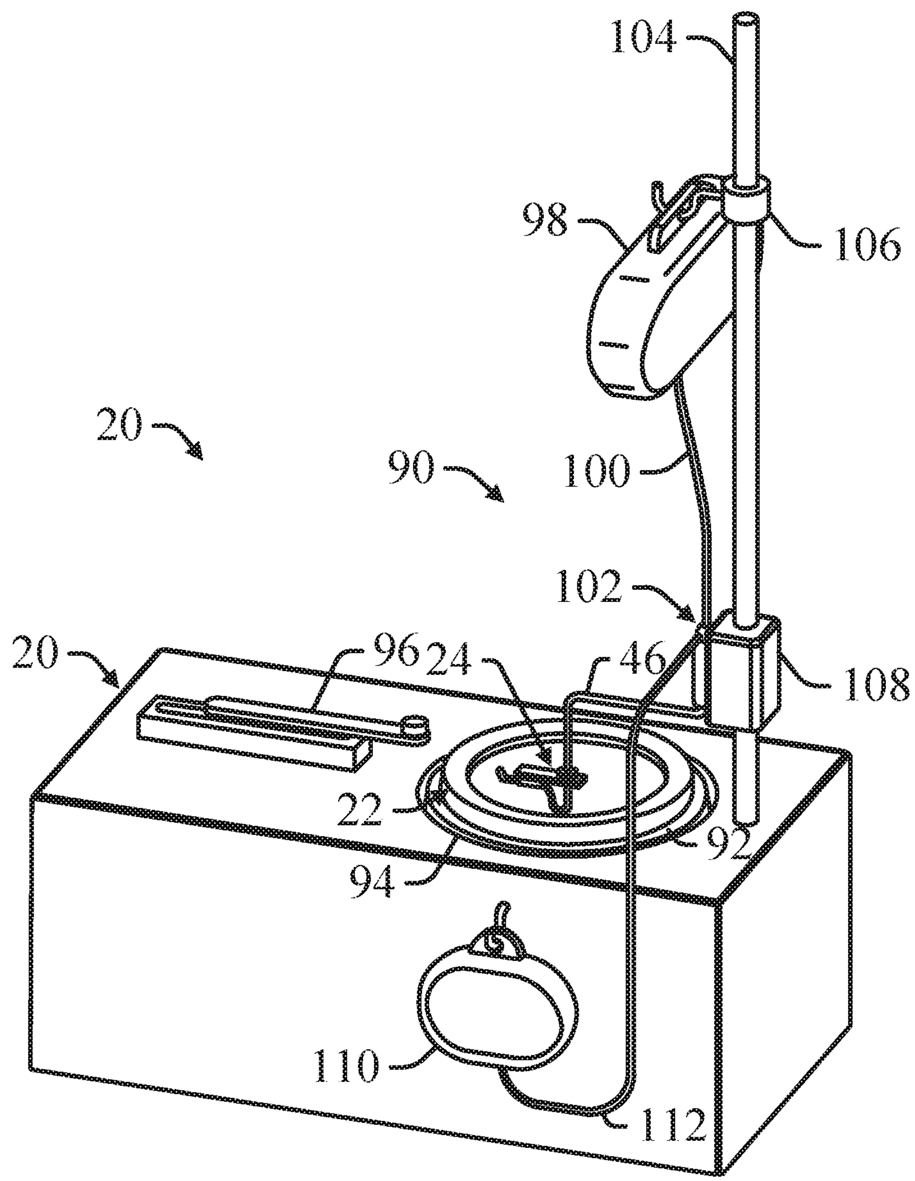
FIG. 13 is a perspective view of a blood washing system having a rotor and a skimmer assembly for separating and collecting red blood cells according to an example of the present disclosure.

As depicted in FIG. 13, in an example, a blood washing system 20 for washing cellular material, according to an example, can include a rotator system 90 for rotating a rotor 22 and adjustably positioning the skimmer assembly 24 within the internal chamber 26. The rotator system 90 can include a rotatable basket 92 positioned adjacent a rotor opening 94 for receiving the rotor 22 into the rotator system 90 and into the rotatable basket 92. The rotatable basket 92 can be engaged to the rotor 22 such that the rotatable basket 92 can be rotated to rotate the rotor 22 received within the rotatable basket 92. In certain examples, the rotatable basket 92 can be operably connected to a rotor lever 96 such that manual rotation of the rotor lever 96 rotates the rotatable basket 92. The rotatable basket 92 can be rotated by a magnetic system, a motor, or other conventional means for rotating the rotatable basket 92 within the rotator system 90.

In an example, the blood washing system 20 can include an input container 98 operably connected to the rotor 22 by an input line 100 for providing the multi-component fluid into the internal chamber 26. The rotor system 90 can include a valve assembly 102 selectively connected to one of the feed tube 38 and the withdrawal outlet 46 for directing the multi-component fluid into the internal chamber 26. As depicted in FIG. 13, in an example, the rotator system 90 can include a positioning rod 104 for adjustably positioning the input container 98 relative to the rotor 22. The rotator system 90 can include an input coupling 106 that can be engaged to the input container 98 and moveable along the positioning rod 104 to elevate or lower the input container 98 relative to the rotor 22. In this configuration, the input container 98 can be elevated above the rotor 22 such that multi-fluid component is fed into the rotor 22 by gravity. In an example, the valve assembly 102 can include a valve coupling 108 moveable along the positioning rod 104 to elevate or lower the valve assembly 102 relative to the rotor 22.

In an example, the output container 110 can be operably connected to the withdrawal outlet 46 by an output line 112 for receiving selected fractions collected by the skimmer assembly 24. The output container 110 can be positioned below the rotor 22 such that collected selected fractions drain into the output container 110 by gravity. In an example, the rotation of the rotor 22 at the slower second speed can force the selected fraction into the skimmer assembly 24 to facilitate flow of the selected fraction through the skimmer assembly 24 and into the output container 110.

Figure 14:
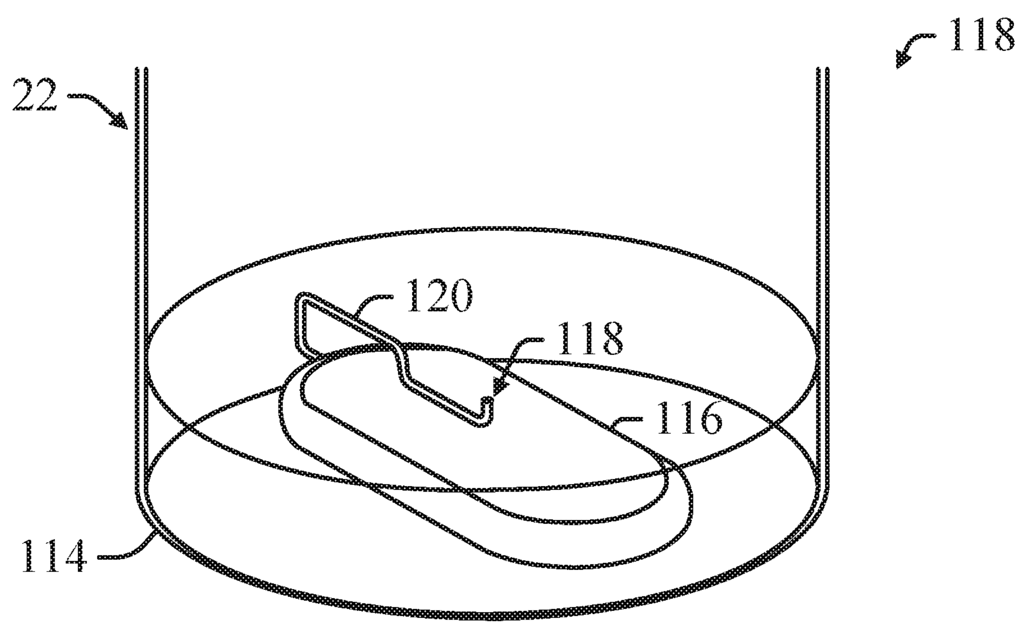
FIG. 14 is a schematic view of a rotor having an integrated collection container according to an example of the present disclosure.

As depicted in FIG. 14, the rotor 22 can include a bottom cap 114 cooperating with the rotor 22 to define a container chamber 116 for receiving an output container 110. The bottom cap 114 can be removably coupled to the rotor 22 to position the container chamber 116 adjacent to an outlet drain 118 in the rotor 22 for accessing the internal chamber 26. The container chamber 116 can be coupled to the outlet drain 118 by an outlet line 120. The rotor 102 and the bottom cap 114 can enclose the output container 110 to permit the output container 110 to rotate with the rotor 22 during separation of the multi-component material to permit collection of a selected fraction.

Figure 15:
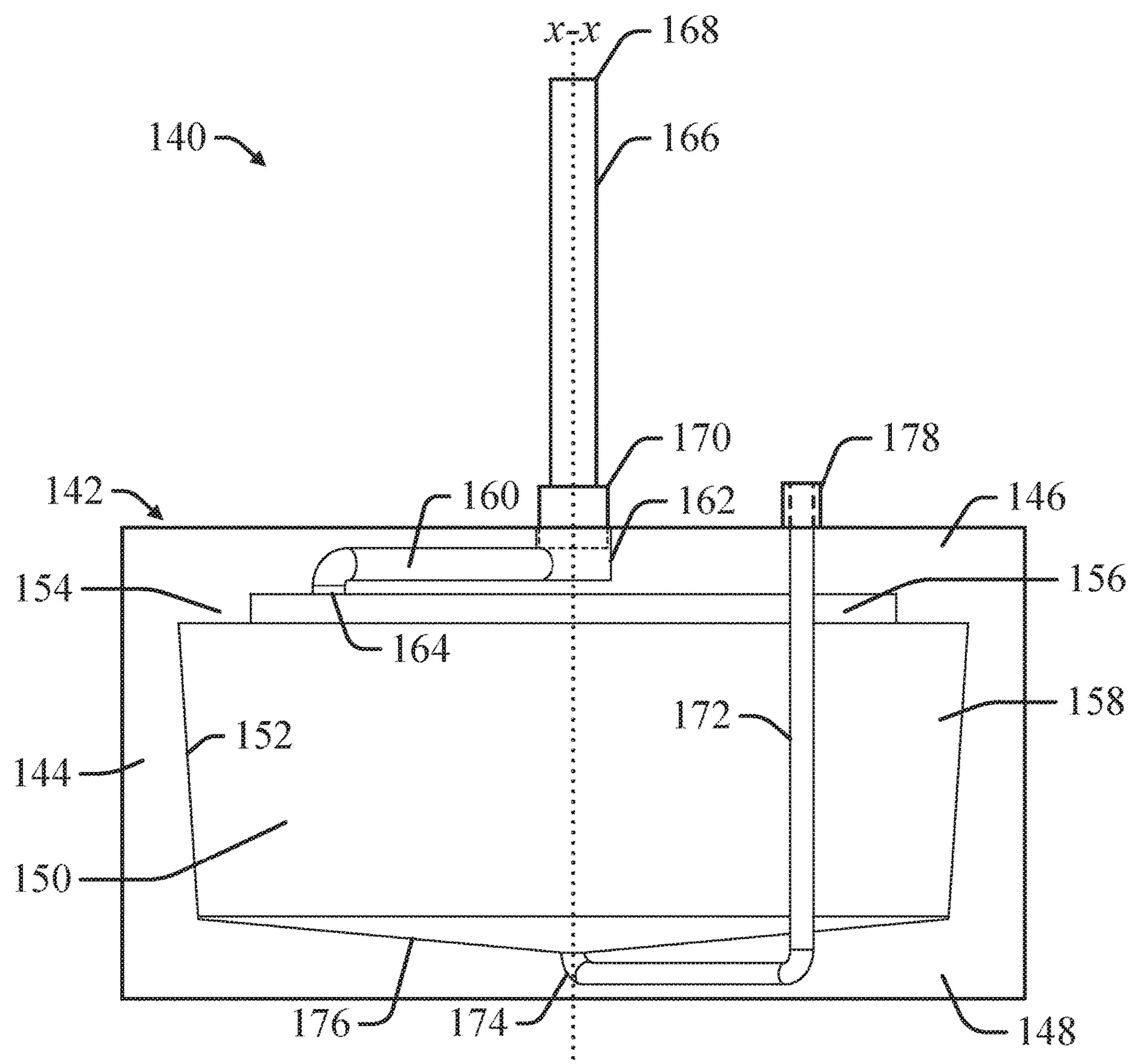
FIG. 15 is a schematic side view of a blood washing system according to an example of the present disclosure.
Figure 16:
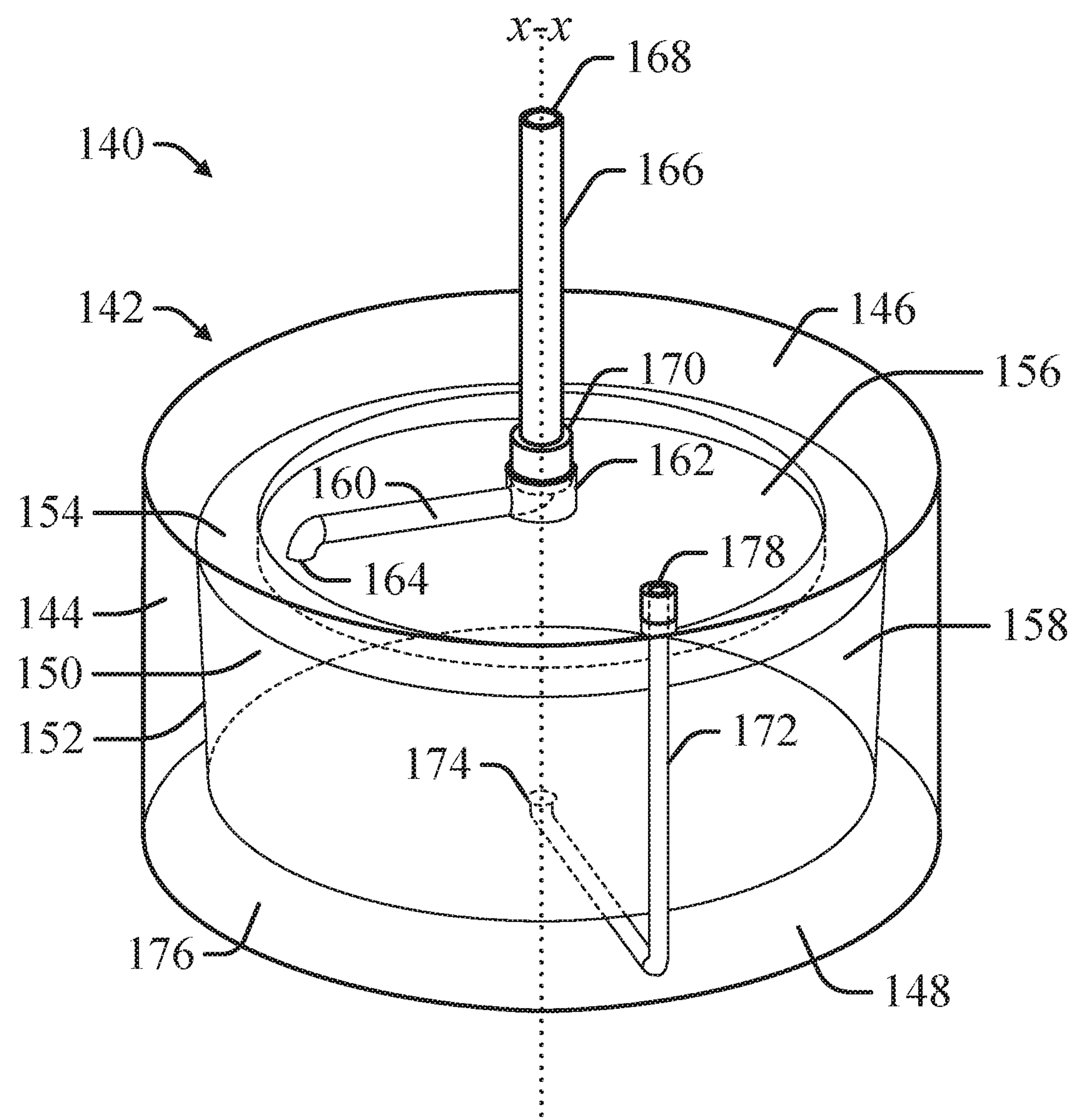
FIG. 16 is a schematic side perspective view of the blood washing system depicted in FIG. 15.

As depicted in FIGS. 15-16, a blood washing system 140 for washing cellular material, according to an example, can include a rotor 142 for fractionating a multi-component fluid, washing at least one fraction, and selectively withdrawing a selected fraction from the rotor 142. The rotor 142 can include at least a radial wall 144 extending from a top wall 146 and a bottom wall 148 to define an internal chamber 150. The rotor 142 can receive into the internal chamber 150 a multi-component fluid, such as a whole blood sample, a wash solution comprising suspended cellular material, or other multi-component fluids containing solid material suspended in a fluid. In an example, the radial wall 144 can have a slanted face 152 for funneling material toward the bottom of the internal chamber 150. In an example, the rotor 142 can include an inwardly projecting shelf 154 positioned at the top of the internal chamber 150. The inwardly projecting shelf 154 defines a reduced diameter portion 156 positioned above a primary portion 158 of the internal chamber 150.

In an example, the blood washing system 140 can include an access tube 160 extending through the top wall 146 of the rotor 142 from an exterior entry port 162 to an access port 164 in the internal chamber 150. A feed tube 166 having a feed orifice 168 can be fluidly connected to the entry port 162 to provide a multi-component fluid into the internal chamber 150. The feed orifice 168 can be operably connected to a pump (not shown), syringe or another device for supplying or withdrawing a multi-component fluid. In at least one example, at least one fraction of the multi-component fluid can be withdrawn from the internal chamber 150 through the access port 164 and feed tube 166.

In operation, the rotor 142 can be rotated about the rotational axis x-x at a first speed to fractionate the multi-component fluid within the internal chamber 150 into a plurality of fractions. The denser fluid and solid fractions are pushed further outward radially from the rotational axis x-x by the rotation of the rotor 142 while the less dense fluid fractions remain closer to the rotational axis x-x. The blood washing system 140 can include a rotating seal 170 for maintaining the connection between the feed tube 166 and the entry port 162 during rotation of the rotor 142. The plurality of fractions can comprise at least one solid fraction containing the solid material and at least one liquid fraction containing the liquid material. In certain examples, the plurality of fractions can comprise multiple liquid fractions having different densities. A brake can be applied to the rotor 142 to stop rotation of the rotor 142 or to rotate the rotor 142 at a second speed slower than the first speed causing the fractions to settle within the internal chamber 150 with the denser fluids and solids settling toward the bottom wall 148. The denser fluids and solids of the fractionated components settle toward the bottom wall 148 where the lighter fluids of the fractionated components settle above the denser fractionated components. The selected fraction (e.g. a liquid fraction) can be aspirated from the reduced diameter portion 156 of the internal chamber 150 through the access port 164, wherein the inwardly projecting shelf 154 retains a portion of the fractions (e.g. a solid fraction) within the primary portion 158 of the internal chamber 150. The access port 164 can be fluidly connected to the reduced diameter portion 156 such that the reduced diameter portion 156 creates a headspace above the retained fractions permitting aspiration of the wash fluids leaving the internal chamber 150. In this configuration, the aspiration of the wash fluids minimizes disruption of solid fractions retained within the primary portion 158 of the internal chamber 150.

Wash fluid can be fed through the feed tube 166 into the internal chamber 150 to wash the retained fractions within the primary portion 158 of the internal chamber 150. In an example, the access port 164 can be offset from the rotational axis x-x such that the rotor 142 can be rotated at a third speed to further distribute the wash fluid. Excess wash fluid can be withdrawn through the feed tube 166 via the access port 164.

In an example, the blood washing system 140 can include a withdrawal tube 172 fluidly connected to a withdrawal port 174 in the bottom wall 148 of the rotor 142. The withdrawal tube 172 can withdraw denser fluid or solid fractions of the multi-component fluid that settles on the bottom wall 148 of the rotor 142 following fractionation. The bottom wall 148 can include a slanted surface 176 with the withdrawal port 174 positioned at an apex such that denser fluids or solid fractions are funneled toward the withdrawal port 174 as the material is withdrawn through the withdrawal tube 172. The withdrawal tube 172 can extend through the bottom wall 148 and the radial wall 144 to an exterior opening 178 in the top wall 146. A pump, syringe, or another device for withdrawing fluids and solids can be connected to the exterior opening 178 to withdraw fluid or solid fractions contained within the primary portion 158 of the internal chamber 150 through the withdrawal port 174.

Figure 17:
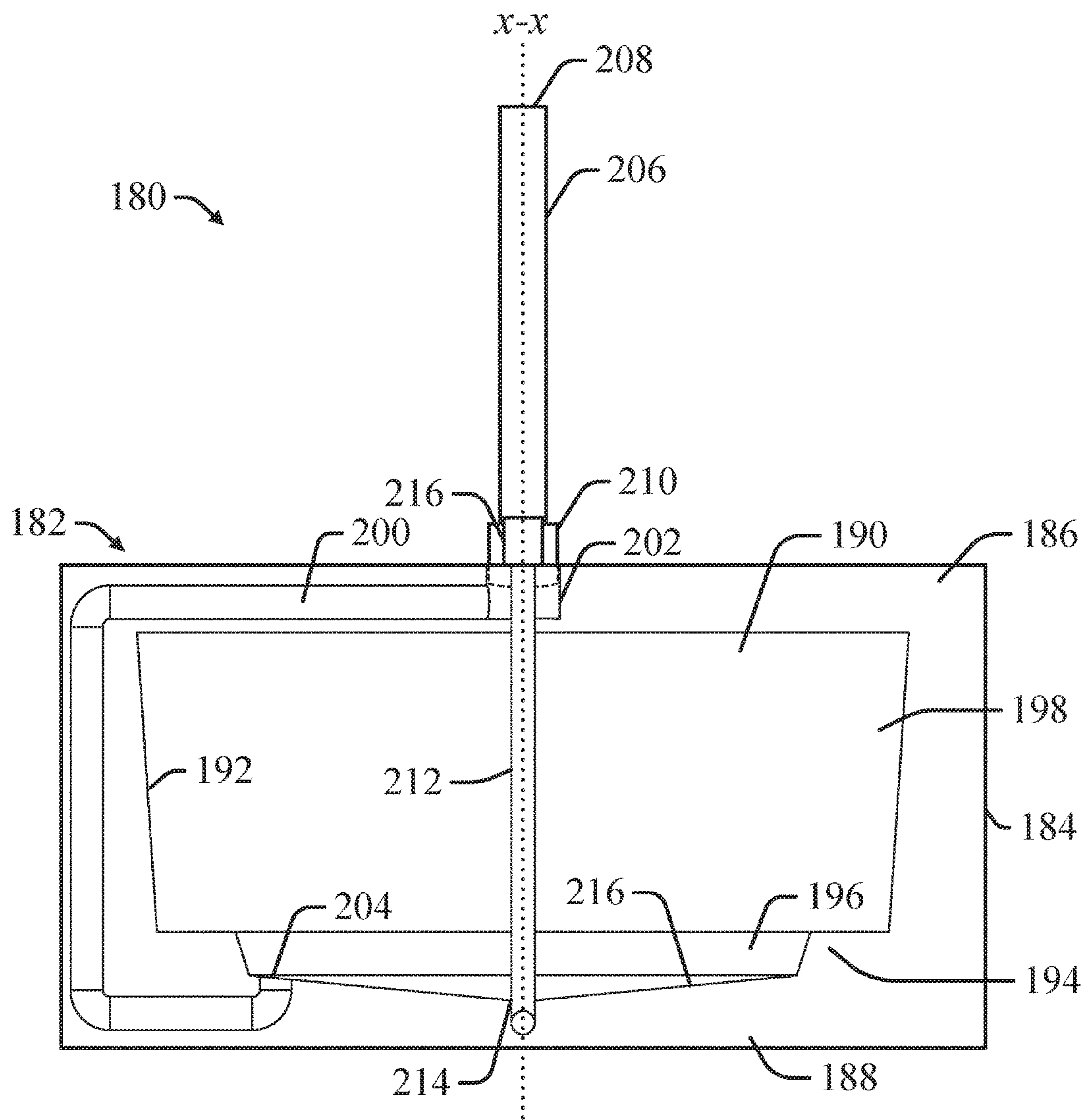
FIG. 17 is a schematic side view of a blood washing system according to an example of the present disclosure.

As depicted in FIG. 17, a blood washing system 180 for washing cellular material, according to an example, can include a rotor 182 for fractionating a multi-component fluid, washing at least one fraction, and selectively withdrawing a selected fraction from the rotor 182. The rotor 182 can include at least a radial wall 184 extending from a top wall 186 and a bottom wall 188 to define an internal chamber 190. The rotor 182 can receive into the internal chamber 190 a multi-component fluid, such as a whole blood sample, a wash solution comprising suspended cellular material, or other multi-component fluids containing solid material suspended in a fluid. In an example, the radial wall 184 can have a slanted face 192 for funneling material toward the bottom of the internal chamber 190. In an example, the rotor 182 can include an inwardly projecting shelf 194 positioned at the bottom of the internal chamber 190. The inwardly projecting shelf 194 defines a reduced diameter portion 196 positioned below a primary portion 198 of the internal chamber 190.

In an example, the blood washing system 180 can include an access tube 200 extending from an exterior entry port 202 through the top wall 186 and the radial wall 184 to an access port 204 into the internal chamber 190. As illustrated in FIG. 17, the access port 204 can be positioned at the bottom of the internal chamber 190. A feed tube 206 having a feed orifice 208 can be fluidly connected to the entry port 202 to provide a multi-component fluid into the internal chamber 190. The feed orifice 208 can be operably connected to a pump (not shown), syringe or another device for supplying a multi-component fluid. In at least one example, at least one fraction of the multi-component fluid can be withdrawn from the internal chamber 190 through the access port 204 and feed tube 206.

In operation, the rotor 182 can be rotated about the rotational axis x-x at a first speed to fractionate the multi-component fluid within the internal chamber 190 into a plurality of fractions. The denser fluid and solid fractions are pushed further outward radially from the rotational axis x-x by the rotation of the rotor 182 while the less dense fluid fractions remain closer to the rotational axis x-x. The blood washing system 180 can include a rotating seal 210 for maintaining the connection between the feed tube 206 and the entry port 202 during rotation of the rotor 182. The plurality of fractions can comprise at least one solid fraction containing the solid material and at least one liquid fraction containing the liquid material. In certain examples, the plurality of fractions can comprise multiple liquid fractions having different densities. A brake can be applied to the rotor 182 to stop rotation of the rotor 182 or to rotate the rotor 182 at a second speed slower than the first speed causing the fractions to settle within the internal chamber 190 with the denser fluids and solids settling toward the bottom wall 188. The lighter fluids of the fractionated components can settle above the denser fractionated components.

Wash fluid can be fed through the feed tube 206 into the internal chamber 190 to wash the retained fractions within the primary portion 198 of the internal chamber 190. The access port 204 can be fluidly connected to the reduced diameter portion 196 such that the wash fluid percolates through the retained fractions within the primary portion 198 of the internal chamber 190. The wash fluids are percolated at a rate such that the solid fractions remain within the primary portion 198 of the internal chamber 190 during percolation of the wash fluids.

In an example, the blood washing system 180 can include a withdrawal tube 212 fluidly connected to a withdrawal port 214 in the bottom wall 188 of the rotor 182. The withdrawal tube 212 can withdraw denser fluid or solid fractions of the multi-component fluid that settles on the bottom wall 188 of the rotor 182 following fractionation. The bottom wall 188 can include a slanted surface 216 with the withdrawal port 214 positioned at an apex such that denser fluids or solid fractions are funneled toward the withdrawal port 214 as the material is withdrawn through the withdrawal tube 212. The withdrawal tube 212 can extend through the bottom wall 188 and the radial wall 184 to an exterior opening 218 in the top wall 146. A pump, syringe, or another device for withdrawing fluids and solids can be connected to the exterior opening 218 to withdraw fluid or solid fractions contained within the primary portion 198 of the internal chamber 150 through the withdrawal port 214.

As depicted in FIGS. 18 and 19A-C, a blood washing system 220 for separating and washing cellular material, according to an example, can include a rotor 222 for fractionating a multi-component fluid, washing at least one fraction, and selectively withdrawing a selected fraction from the rotor 222. The rotor 222 can include at least a radial wall 224 extending from a top wall 226 and a bottom wall 228 to define an internal chamber 230. The rotor 222 can receive into the internal chamber 230 a multi-component fluid, such as a whole blood sample, a wash solution comprising suspended cellular material, or other multi-component fluids containing solid material suspended in a fluid. In an example, the radial wall 224 can have a slanted face 232 for funneling material toward the bottom of the internal chamber 230. In an example, the rotor 222 can include an inner wall 234 dividing the internal chamber 230 into an inner portion 236 and an outer portion 238. The inner wall 234 can project from the top wall 226 such that the inner wall 234 is proximate to the bottom surface of the internal chamber 230. The bottom wall 228 and the inner wall 234 cooperate to form a gap fluidly connecting the inner portion 236 and the outer portion 238.

Figure 18:
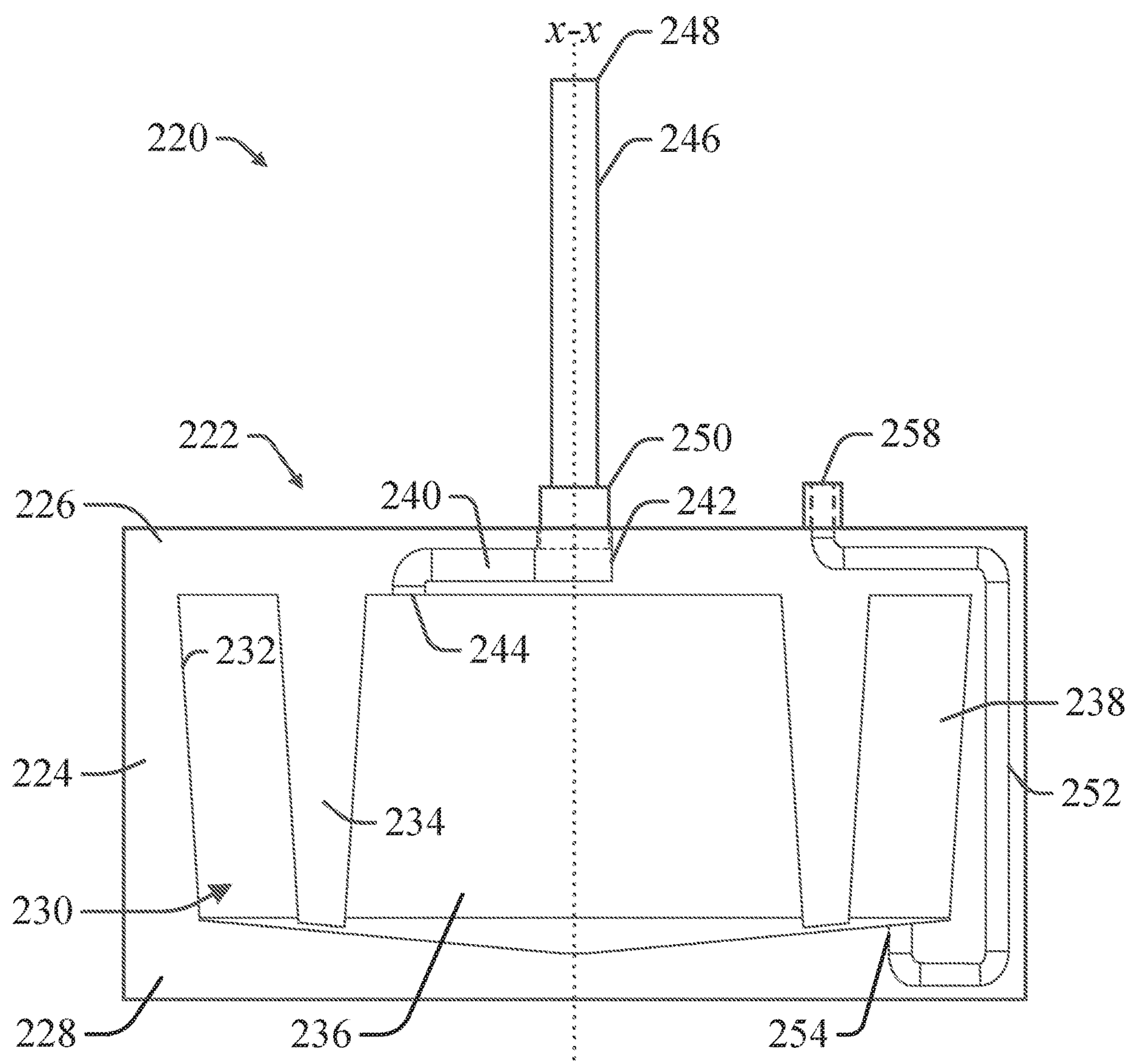
FIG. 18 is a schematic side view of a blood washing system according to an example of the present disclosure.

In an example, the blood washing system 220 can include an access tube 240 extending from an exterior entry port 242 through the top wall 226 and the radial wall 224 to an access port 244 into the internal chamber 230. As illustrated in FIG. 18, the access port 244 can be positioned at the top of the internal chamber 230. A feed tube 246 having a feed orifice 248 can be fluidly connected to the entry port 242 to provide a multi-component fluid into the internal chamber 230. The feed orifice 248 can be operably connected to a pump (not shown), syringe or another device for supplying a multi-component fluid. In at least one example, at least one fraction of the multi-component fluid can be withdrawn from the internal chamber 230 through the access port 244 and feed tube 246.

Figures 19A, 19B, 19C:
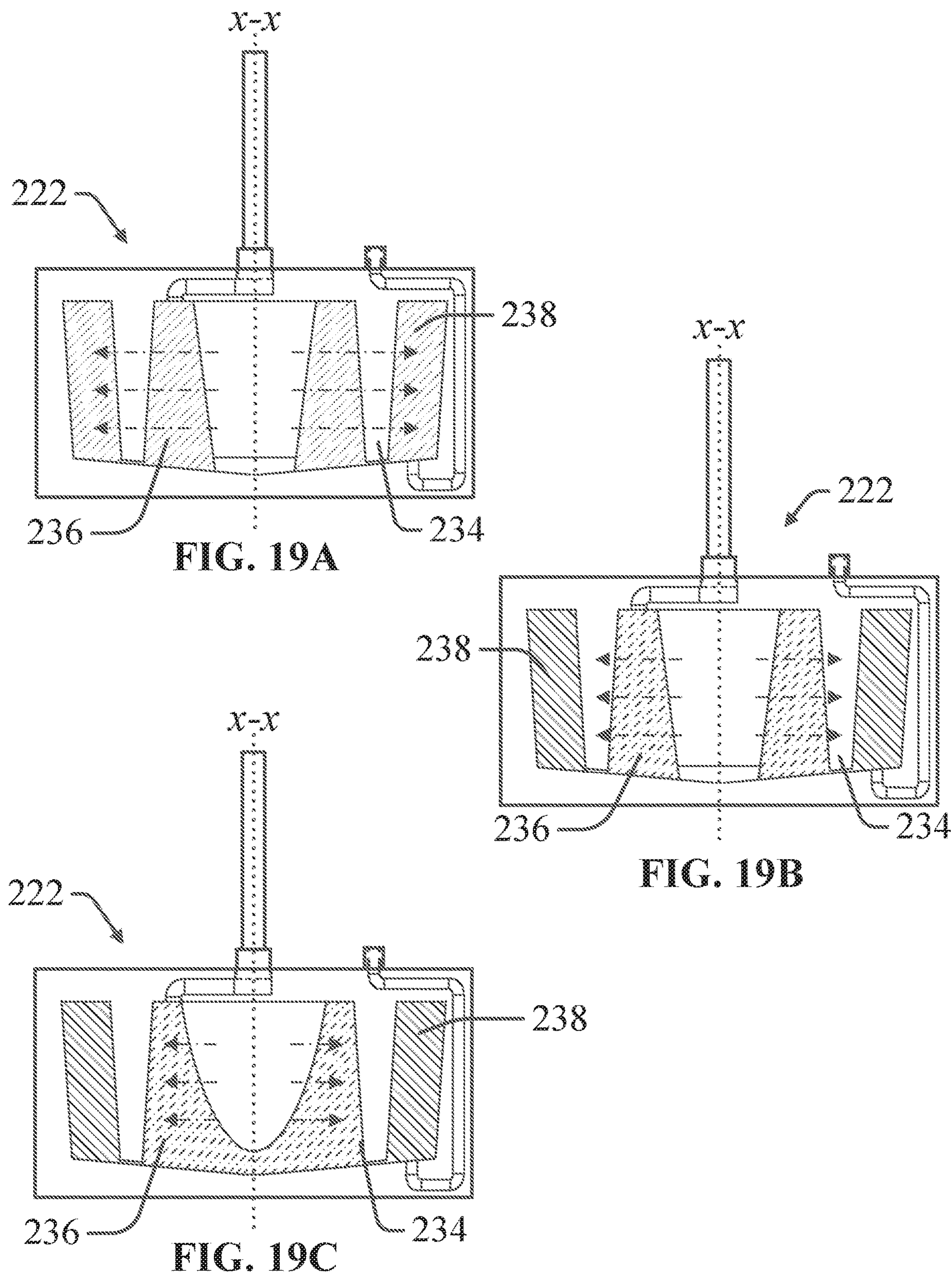
FIG. 19A is a schematic side view of the blood washing system depicted in FIG. 18, wherein a multi-component fluid is being rotated at a first speed to fractionate the multi-component fluid.
FIG. 19B is a schematic side view of the blood washing system depicted in FIG. 18, wherein a multi-component fluid following fractionation of the multi-component fluid.
FIG. 19C is a schematic side view of the blood washing system depicted in FIG. 18, wherein a multi-component fluid is being rotated at a second, slower speed following fractionation of the multi-component fluid.

As illustrated in FIG. 19B, in operation, the rotor 222 can be rotated about the rotational axis x-x at a first speed to fractionate the multi-component fluid within the internal chamber 230 into a plurality of fractions. As illustrated in FIG. 19B, the denser fluid and solid fractions are pushed further outward radially from the rotational axis x-x by the rotation of the rotor 222 while the less dense fluid fractions remain closer to the rotational axis x-x. The denser fluid and solid fraction can pass through the gap between the bottom wall 228 and the inner wall 234 into the outer portion 238 of the internal chamber 230. The lighter fluids can be retained within the inner portion 236 of the internal chamber 230 as shown in FIG. 19B. A brake can be applied to the rotor 222 to slow the rotation of the rotor 222 to a second, slower rotational speed. At the second speed, the lighter fluids within the inner portion 236 can be withdrawn through the access port 224. In an example, additional wash fluids can be fed through the access port 224. In an example, the brake can be applied to the rotor 222 to slow the rotor 222 to a third, slower rotational speed. At the slower rotational speed, fluids can elute from the outer portion 238 back into the inner portion 236 for withdrawal through the access port 234.

In an example, the blood washing system 220 can include a withdrawal tube 252 fluidly connected to a withdrawal port 254 in the bottom wall 228 of the rotor 222. The withdrawal tube 252 can withdraw denser fluid or solid fractions of the multi-component fluid that settles on the bottom wall 228 of the rotor 222 following fractionation. The bottom wall 228 can include a slanted surface 216 oriented toward an apex. The withdrawal tube 252 can extend through the bottom wall 228 and the radial wall 224 to an exterior opening 258 in the top wall 146. A pump, syringe, or another device for withdrawing fluids and solids can be connected to the exterior opening 218 to withdraw fluid or solid fractions contained within the primary portion 198 of the internal chamber 150 through the withdrawal port 214.

Various Notes & Examples

Example 1 is a blood washing system for washing cellular material, comprising: a rotor defining an internal chamber for receiving a multi-component fluid, the rotor being rotatable about a rotational axis at a first speed to fractionate the multi-component fluid into a plurality of fractions; and a skimmer assembly including a withdrawal needle movable within the internal chamber; wherein the withdrawal needle is moveable within the internal chamber to align a withdrawal orifice of the withdrawal needle with a selected fraction of the plurality of fractions for selectively withdrawing the selected fraction through the withdrawal needle.

In Example 2, the subject matter of Example 1 optionally includes wherein the rotor further comprises: a top wall defining an access port for accessing the internal chamber; and a bottom wall opposite the top wall.

In Example 3, the subject matter of Example 2 optionally includes a feed tube having a feed orifice; wherein the feed tube is insertable through the access port such that the feed orifice is positioned proximate the bottom wall.

In Example 4, the subject matter of Example 3 optionally includes wherein the bottom wall further comprises: a tapered rotor floor having a bottom apex centered on the rotational axis; wherein the feed tube is insertable through the access port such that the feed orifice is positioned proximate the bottom apex.

In Example 5, the subject matter of any one or more of Examples 2-4 optionally include wherein the rotor is configured to be rotated at a second speed slower than the first speed such that the plurality of fractions stack on the bottom wall of the rotor along the rotational axis.

In Example 6, the subject matter of Example 5 optionally includes wherein the withdrawal needle is configured to move along at least a movement axis to align the withdrawal orifice with a selected friction; wherein the movement axis is parallel to the rotational axis.

In Example 7, the subject matter of Example 6 optionally includes wherein the rotor further comprises: a washer guide positioned on a sidewall of the rotor; wherein the washer guide is sized to engage the withdrawal needle as the withdrawal needle is moved along the movement axis to limit movement of the withdrawal needle.

In Example 8, the subject matter of any one or more of Examples 6-7 optionally include a withdrawal outlet; and a withdrawal tube connecting the withdrawal needle to the withdrawal outlet; wherein material withdrawn through the withdrawal needle is directed into the withdrawal outlet through the withdrawal tube.

In Example 9, the subject matter of Example 8 optionally includes wherein the withdrawal tube is flexible to permit movement of the withdrawal needle relative to the withdrawal outlet.

In Example 10, the subject matter of Example 9 optionally includes a drive gear having a first diameter; a slave gear having a second diameter and intermeshed with the drive gear; and a skimmer arm coupled to the withdrawal needle and extending from the slave gear such that rotation of the drive gear rotates the skimmer arm in a plane perpendicular to the rotational axis.

In Example 11, the subject matter of Example 10 optionally includes wherein the withdrawal needle further comprises a scoop oriented to capture fluid as the withdrawal needle is rotated within the plane.

In Example 12, the subject matter of any one or more of Examples 9-11 optionally include wherein the skimmer assembly further comprises: a guide sleeve extending through the access port in the rotor; and a cable extending through the sleeve guide and operably connected to the withdrawal needle; wherein the cable can be extended and retracted to move the withdrawal needle within the internal chamber.

In Example 13, the subject matter of any one or more of Examples 9-12 optionally include wherein the skimmer assembly further comprises: a track positioned external of the rotor; and an external magnet moveable along the track; wherein the withdrawal needle includes an internal magnet such that movement of the external magnet along the track moves the withdrawal needle within the internal chamber.

In Example 14, the subject matter of any one or more of Examples 6-13 optionally include a hermetic seal connecting the withdrawal needle to a withdrawal outlet, the hermetic seal including: an outer sleeve coupled to one of the withdrawal outlet and the withdrawal tube, and an inner sleeve coupled to the other of the withdrawal outlet and the withdrawal tube, wherein the inner sleeve is slideably received within the outer sleeve such that connection of the withdrawal needle to the withdrawal outlet during movement of the withdrawal needle along the movement axis.

In Example 15, the subject matter of any one or more of Examples 1-14 optionally include an outer housing defining a rotor chamber for receiving the rotor; wherein the rotor is configured to rotate within the rotor chamber.

In Example 16, the subject matter of Example 15 optionally includes wherein the rotor further comprises: an integrated magnet for inducing rotation of the rotor within the outer housing.

In Example 17, the subject matter of any one or more of Examples 15-16 optionally include wherein the rotor further comprises a height and a diameter.

In Example 18, the subject matter of Example 17 optionally includes wherein the rotor further comprises: an upper bearing surface engaging an upper interior surface of the outer housing during rotation of the rotor to maintain alignment of the rotor with the rotational axis during rotation of the rotor; wherein the diameter of the rotor is greater than the height of the rotor.

In Example 19, the subject matter of any one or more of Examples 15-18 optionally include wherein the rotor further comprises a center post positioned within the internal chamber.

In Example 20, the subject matter of Example 19 optionally includes wherein the outer housing further comprises: a rotational spindle aligned with the rotational axis of the rotor; wherein the center post defines a spindle port for receiving the rotational spindle to maintain alignment of the rotor with the rotational axis during rotation of the rotor.

Example 21 is a method of washing cellular material, comprising: providing a multi-component fluid into an internal chamber of a rotor; rotating the rotor at a first speed to fractionate the multi-component fluid into a plurality of fractions; moving a withdrawal needle within the internal chamber to align a withdrawal orifice of the withdrawal need within a first selected fraction of the plurality of fractions; and withdrawing the first selected fraction through the withdrawal needle.

In Example 22, the subject matter of Example 21 optionally includes inserting a feed tube through an access port in a top wall of the rotor such that a feed orifice of the feed tube is positioned proximate the bottom wall of the rotor; and withdrawing a second selected fraction through the feed tube.

In Example 23, the subject matter of Example 22 optionally includes wherein the second selected fraction is at least one of a solid and a denser fluid than the first selected fraction.

In Example 24, the subject matter of any one or more of Examples 22-23 optionally include wherein the bottom wall further comprises a tapered rotor floor; wherein the second selected fraction is a solid.

In Example 25, the subject matter of any one or more of Examples 22-24 optionally include slowing the rotation of the rotor to a second speed slower than the first speed to cause the plurality of fractions to settle and stack along the rotational axis.

In Example 26, the subject matter of Example 25 optionally includes moving the withdrawal needle along a movement axis to align with the first selected fraction; wherein the movement axis is parallel to the rotational axis.

In Example 27, the subject matter of Example 26 optionally includes positioning a washer within the internal chamber; wherein the washer limits movement of the withdrawal needle along the movement axis.

In Example 28, the subject matter of any one or more of Examples 21-27 optionally include rotating a skimmer arm connected to the withdrawal needle to rotate the withdrawal needle in a plane perpendicular to the rotational axis.

In Example 29, the subject matter of Example 28 optionally includes wherein the withdrawal needle further comprises a scoop oriented to capture fluid as the withdrawal needle is rotated within the plane.

In Example 30, the subject matter of any one or more of Examples 21-29 optionally include connecting a cable to the withdrawal needle; and manipulating the cable to move the withdrawal needle within the internal chamber.

In Example 31, the subject matter of any one or more of Examples 21-30 optionally include positioning a track external to the rotor; moving an external magnet along the track; wherein the withdrawal needle includes an internal magnet such that movement of the external magnet along the track moves the withdrawal needle within the internal chamber.

Example 32 is a blood washing system for washing cellular material, comprising: a rotor having a radial wall extending from a bottom wall to a top wall to define an internal chamber for receiving a multi-component fluid, the radial wall further including an inwardly projecting shelf at the top wall to define a reduced diameter portion above a primary portion of the internal chamber; wherein the rotor being rotatable about a rotational axis at a first speed to fractionate the multi-component fluid into a plurality of fractions such that denser fractions are retained within the primary portion by the inwardly projecting shelf.

In Example 33, the subject matter of Example 32 optionally includes wherein the rotor further comprises: an access tube extending through the top wall from an exterior entry port to an access port in the internal chamber.

In Example 34, the subject matter of Example 33 optionally includes wherein the access port is positioned on a top surface of the internal chamber.

In Example 35, the subject matter of any one or more of Examples 33-34 optionally include wherein the blood washing system further comprises: a feed tube having a feed orifice, the feed tube configured to be coupled to the exterior entry port.

In Example 36, the subject matter of Example 35 optionally includes wherein the access port is configured to withdraw at least one fraction of the plurality of fractions from the internal chamber.

In Example 37, the subject matter of any one or more of Examples 35-36 optionally include wherein the feed orifice is configured to be coupled to a device for supplying or withdrawing fluid from the internal chamber of the rotor.

In Example 38, the subject matter of any one or more of Examples 35-37 optionally include a rotating seal fluidly connecting the feed tube to the access tube as the rotor is rotated.

In Example 39, the subject matter of any one or more of Examples 32-38 optionally include wherein the rotor further comprising: a withdrawal tube extending through the top wall from an exterior opening to a withdrawal port in the internal chamber.

In Example 40, the subject matter of Example 39 optionally includes wherein the withdrawal port positioned on a bottom surface of the internal chamber.

In Example 41, the subject matter of Example 40 optionally includes wherein the withdrawal tube extends through the bottom wall and radial wall to the top wall.

In Example 42, the subject matter of any one or more of Examples 40-41 optionally include wherein the bottom wall of the rotor includes a slanted surface slanted to an apex; wherein the withdrawal port is positioned at the apex.

Example 43 is a blood washing system for washing cellular material, comprising: a rotor having a radial wall extending from a bottom wall to a top wall to define an internal chamber for receiving a multi-component fluid, the radial wall further including an inwardly projecting shelf at the bottom wall to define a reduced diameter portion below a primary portion of the internal chamber; wherein the rotor being rotatable about a rotational axis at a first speed to fractionate the multi-component fluid into a plurality of fractions such that denser fractions are retained on the bottom wall of the rotor.

In Example 44, the subject matter of Example 43 optionally includes wherein the rotor further comprises: an access tube extending through the top wall from an exterior entry port to an access port in the internal chamber.

In Example 45, the subject matter of Example 44 optionally includes wherein the access port is positioned on a bottom surface of the internal chamber.

In Example 46, the subject matter of any one or more of Examples 44-45 optionally include wherein the blood washing system further comprises: a feed tube having a feed orifice, the feed tube configured to be coupled to the exterior entry port.

In Example 47, the subject matter of Example 46 optionally includes wherein the access port is configured to provide wash fluid into the internal chamber to percolate the wash fluid through at least one fraction of the plurality of fractions.

In Example 48, the subject matter of any one or more of Examples 46-47 optionally include wherein the feed orifice is configured to be coupled to a device for supplying or withdrawing fluid from the internal chamber of the rotor.

In Example 49, the subject matter of any one or more of Examples 46-48 optionally include a rotating seal fluidly connecting the feed tube to the access tube as the rotor is rotated.

In Example 50, the subject matter of any one or more of Examples 43-49 optionally include wherein the rotor further comprising: a withdrawal tube extending through the top wall from an exterior opening to a withdrawal port in the internal chamber.

In Example 51, the subject matter of Example 50 optionally includes wherein the withdrawal port positioned on a bottom surface of the internal chamber.

In Example 52, the subject matter of Example 51 optionally includes wherein the withdrawal tube extends through the bottom wall and radial wall to the top wall.

In Example 53, the subject matter of any one or more of Examples 51-52 optionally include wherein the bottom wall of the rotor includes a slanted surface slanted to an apex; wherein the withdrawal port is positioned at the apex.

Example 54 is a blood washing system for washing cellular material, comprising: a rotor rotatable about a rotational axis, the rotor including: a radial wall extending from a bottom wall to a top wall to define an internal chamber, and an inner wall projecting from the top wall such to divide the internal chamber into an inner portion and an outer portion, wherein the inner wall and bottom wall cooperate to define a gap connecting the inner portion and the outer portion; wherein the rotor being rotatable about the rotational axis at a first speed to fractionate the multi-component fluid into a plurality of the fractions such that lighter fractions are retained in the inner portion and denser fractions move into the outer portion through the gap.

In Example 55, the subject matter of Example 54 optionally includes wherein the rotor further comprises: an access tube extending through the top wall from an exterior entry port to an access port in the internal chamber.

In Example 56, the subject matter of Example 55 optionally includes wherein the access port is positioned on a top surface of the internal chamber at the inner portion of the internal chamber.

In Example 57, the subject matter of any one or more of Examples 55-56 optionally include wherein the blood washing system further comprises: a feed tube having a feed orifice, the feed tube configured to be coupled to the exterior entry port.

In Example 58, the subject matter of Example 57 optionally includes wherein the access port is configured to withdraw at least one fraction of the plurality of fractions from inner portion of the internal chamber.

In Example 59, the subject matter of any one or more of Examples 57-58 optionally include wherein the feed orifice is configured to be coupled to a device for supplying or withdrawing fluid from the internal chamber of the rotor.

In Example 60, the subject matter of any one or more of Examples 57-59 optionally include a rotating seal fluidly connecting the feed tube to the access tube as the rotor is rotated.

In Example 61, the subject matter of any one or more of Examples 54-60 optionally include wherein the rotor further comprising: a withdrawal tube extending through the top wall from an exterior opening to a withdrawal port in the internal chamber.

In Example 62, the subject matter of Example 61 optionally includes wherein the withdrawal port is fluidly connected to the outer portion of the internal chamber.

In Example 63, the subject matter of Example 62 optionally includes wherein the withdrawal tube extends through the bottom wall and radial wall to the top wall.

In Example 64, the subject matter of any one or more of Examples 62-63 optionally include wherein the bottom wall of the rotor includes a slanted surface slanted to an apex.

Each of these non-limiting examples can stand on its own, or can be combined in any permutation or combination with any one or more of the other examples.

The above-detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. A blood washing system for washing cellular material, comprising:
- a rotor defining an internal chamber for receiving a multi-component fluid, the rotor being rotatable about a rotational axis at a first speed to fractionate the multi-component fluid into a plurality of fractions; and
- a skimmer assembly including a withdrawal needle movable within the internal chamber;
- wherein the withdrawal needle is moveable within the internal chamber to align a withdrawal orifice of the withdrawal needle with a selected fraction of the plurality of fractions for selectively withdrawing the selected fraction through the withdrawal needle, wherein the withdrawal needle is configured to move along a movement axis to align the withdrawal orifice with a selected fraction, and wherein the movement axis is parallel to the rotational axis;
- wherein the rotor is configured to be rotated at a second speed slower than the first speed such that the plurality of fractions stack on a bottom wall of the rotor along the rotational axis, wherein the rotor further comprises:
- a top wall defining an access port for accessing the internal chamber; and
- the bottom wall opposite the top wall.

2. The blood washing system of claim 1, further comprising:
- a feed tube having a feed orifice;
- wherein the feed tube is insertable through the access port such that the feed orifice is positioned proximate the bottom wall.

3. The blood washing system of claim 2, wherein the bottom wall further comprises:
- a tapered rotor floor having a lowest point of the bottom wall centered on the rotational axis;
- wherein the feed tube is insertable through the access port such that the feed orifice is positioned proximate the lowest point of the bottom wall.

4. A blood washing system for washing cellular material, comprising:
- a rotor defining an internal chamber for receiving a multi-component fluid, the rotor being rotatable about a rotational axis at a first speed to fractionate the multi-component fluid into a plurality of fractions; and
- a skimmer assembly including a withdrawal needle movable within the internal chamber;
- wherein the withdrawal needle is moveable within the internal chamber to align a withdrawal orifice of the withdrawal needle with a selected fraction of the plurality of fractions for selectively withdrawing the selected fraction through the withdrawal needle, wherein the withdrawal needle is configured to move along at least a movement axis to align the withdrawal orifice with a selected fraction, and wherein the movement axis is parallel to the rotational axis;
- wherein the rotor is configured to be rotated at a second speed slower than the first speed such that the plurality of fractions stack on a bottom wall of the rotor along the rotational axis, the rotor further comprises:
- a top wall defining an access port for accessing the internal chamber;
- the bottom wall opposite the top wall; and
- a washer guide positioned on a sidewall of the rotor;
- wherein the washer guide is sized to engage the withdrawal needle as the withdrawal needle is moved along the movement axis to limit movement of the withdrawal needle.

5. The blood washing system of claim 1, further comprising:
- a withdrawal outlet; and
- a withdrawal tube connecting the withdrawal needle to the withdrawal outlet;
- wherein material withdrawn through the withdrawal needle is directed into the withdrawal outlet through the withdrawal tube.

6. The blood washing system of claim 5, wherein the withdrawal tube is flexible to permit movement of the withdrawal needle relative to the withdrawal outlet.

7. The blood washing system of claim 6, further comprising:
- a drive gear having a first diameter;
- a slave gear having a second diameter and intermeshed with the drive gear; and
- a skimmer arm coupled to the withdrawal needle and extending from the slave gear such that rotation of the drive gear rotates the skimmer arm in a plane perpendicular to the rotational axis.

8. The blood washing system of claim 7, wherein the withdrawal needle further comprises a scoop oriented to capture fluid as the withdrawal needle is rotated within the plane.

9. The blood washing system of claim 6, wherein the skimmer assembly further comprises:

a guide sleeve extending through the access port in the rotor; and a cable extending through the sleeve guide and operably connected to the withdrawal needle;

wherein the cable can be extended and retracted to move the withdrawal needle within the internal chamber.

10. The blood washing system of claim 6, wherein the skimmer assembly further comprises:

a track positioned external of the rotor; and an external magnet moveable along the track;

wherein the withdrawal needle includes an internal magnet such that movement of the external magnet along the track moves the withdrawal needle within the internal chamber.

11. The blood washing system of claim 1, further comprising:

a hermetic seal connecting the withdrawal needle to a withdrawal outlet, the hermetic seal including:

an outer sleeve coupled to one of the withdrawal outlet and the withdrawal tube, and an inner sleeve coupled to the other of the withdrawal outlet and the withdrawal tube, wherein the inner sleeve is slideably received within the outer sleeve such that connection of the withdrawal needle to the withdrawal outlet during movement of the withdrawal needle along the movement axis is maintained.

12. The blood washing system of claim 1, further comprising:

an outer housing defining a rotor chamber for receiving the rotor;

wherein the rotor is configured to rotate within the rotor chamber.

13. The blood washing system of claim 12, wherein the rotor further comprises:

an integrated magnet for inducing rotation of the rotor within the outer housing.

14. The blood washing system of claim 12, wherein the rotor further comprises a height and a diameter.

15. The blood washing system of claim 14, wherein the rotor further comprises:

an upper bearing surface engaging an upper interior surface of the outer housing during rotation of the rotor to maintain alignment of the rotor with the rotational axis during rotation of the rotor;

wherein the diameter of the rotor is greater than the height of the rotor.

16. The blood washing system of claim 12, wherein the rotor further comprises a center post positioned within the internal chamber.

17. The blood washing system of claim 16, wherein the outer housing further comprises:

a rotational spindle aligned with the rotational axis of the rotor;

wherein the center post defines a spindle port for receiving the rotational spindle to maintain alignment of the rotor with the rotational axis during rotation of the rotor.

18. A blood washing system for washing cellular material, comprising:

a rotor defining an internal chamber for receiving a multi-component fluid, the rotor being rotatable about a rotational axis at a first speed to fractionate the multi-component fluid into a plurality of fractions;

a skimmer assembly including a withdrawal needle movable within the internal chamber;

wherein the withdrawal needle is moveable within the internal chamber to align a withdrawal orifice of the withdrawal needle with a selected fraction of the plurality of fractions for selectively withdrawing the selected fraction through the withdrawal needle;

a drive gear having a first diameter;

a slave gear having a second diameter and intermeshed with the drive gear; and a skimmer arm coupled to the withdrawal needle and extending from the slave gear such that rotation of the drive gear rotates the skimmer arm in a plane perpendicular to the rotational axis of the rotor, wherein the withdrawal needle further comprises a scoop oriented to capture fluid as the withdrawal needle is rotated within the plane.

* * * * *